(12) United States Patent
Sekura

(10) Patent No.: US 7,639,120 B2
(45) Date of Patent: *Dec. 29, 2009

(54) PRESCRIPTION COMPLIANCE DEVICE AND METHOD OF USING DEVICE

(76) Inventor: Ronald D. Sekura, c/o Biotechnology Assessment Services, Inc., 7413 Ottenbrook Ter., Rockville, MD (US) 20855

( * ) Notice: Subject to any disclaimer, the term of this patent is extended or adjusted under 35 U.S.C. 154(b) by 29 days.

This patent is subject to a terminal disclaimer.

(21) Appl. No.: 11/957,191

(22) Filed: Dec. 14, 2007

(65) Prior Publication Data

US 2008/0215289 A1 Sep. 4, 2008

Related U.S. Application Data

(63) Continuation of application No. 10/481,727, filed as application No. PCT/US02/19940 on Jun. 24, 2002, now Pat. No. 7,330,101.

(60) Provisional application No. 60/299,761, filed on Jun. 22, 2001.

(51) Int. Cl.
*G08B 1/00* (2006.01)
(52) U.S. Cl. ............................. 340/309.4; 221/2; 221/3; 221/15; 368/10
(58) Field of Classification Search .............. 340/309.4; 221/2, 3, 15; 368/10
See application file for complete search history.

(56) References Cited

U.S. PATENT DOCUMENTS

| | | | |
|---|---|---|---|
| 4,504,153 A | 3/1985 | Schollmeyer et al. |
| 4,588,303 A | 5/1986 | Wirtschafter et al. |
| 4,626,105 A | 12/1986 | Miller |
| 5,020,037 A | 5/1991 | Raven |
| 5,088,056 A | 2/1992 | McIntosh |
| 5,408,443 A | 4/1995 | Weinberger |
| 5,495,961 A | 3/1996 | Maestre |

(Continued)

FOREIGN PATENT DOCUMENTS

DE 100 46 762 A1 5/2001

(Continued)

*Primary Examiner*—John A Tweel, Jr.
(74) *Attorney, Agent, or Firm*—Oblon, Spivak, McClelland, Maier & Neustadt, L.L.P.

(57) ABSTRACT

A prescription compliance device which aids patients in complying with instructions given by a physician for taking prescription medication. The device reminds a patient when the next dose of medication is to be taken and indicates whether a specified dose has been taken. The device includes a microcontroller, a display, a program memory for storing pre-programmed medication-taking regimens for single and multiple medications, a real time clock, a selector for selecting one of the regimens and for programming the device as to the time and day on which a first dose of medication is to be taken, a display which alternately displays the current time and a time at which a next dose of medication is to be taken and an alarm which alerts the patient at times when a dose of medication is to be taken. The selector includes an event switch which is activated by the patient after taking a dose of medication so as to record the taking of medication and to cause the microcontroller to effect the display of the next time at which a dose of medication is to be taken. A memory may also be included to record the times at which a patient takes doses of medication. The device also includes a remote programming feature via a wireless link.

29 Claims, 38 Drawing Sheets

U.S. PATENT DOCUMENTS

| | | |
|---|---|---|
| 5,522,525 A | 6/1996 | McLaughlin |
| 5,554,967 A | 9/1996 | Cook et al. |
| 5,625,334 A | 4/1997 | Compton |
| 5,703,786 A | 12/1997 | Conkright |
| 5,724,021 A | 3/1998 | Perrone |
| 5,805,051 A | 9/1998 | Hermann et al. |
| 5,990,782 A | 11/1999 | Lee |
| 6,018,289 A | 1/2000 | Sekura et al. |
| 6,130,860 A | 10/2000 | Suzuki |
| 6,169,707 B1 | 1/2001 | Newland |
| 6,198,695 B1 | 3/2001 | Kirton |
| 6,201,768 B1 | 3/2001 | De Meyer et al. |
| 6,335,907 B1 | 1/2002 | Momich et al. |
| 6,529,446 B1 | 3/2003 | De La Huerga |
| 6,687,190 B2 | 2/2004 | Momich et al. |
| 6,961,285 B2 * | 11/2005 | Niemiec et al. ............... 368/10 |
| 7,330,101 B2 * | 2/2008 | Sekura .................... 340/309.4 |

FOREIGN PATENT DOCUMENTS

| | | |
|---|---|---|
| EP | 1 016 399 A2 | 7/2000 |
| EP | 1 087 322 A2 | 3/2001 |
| JP | 55-500803 | 10/1980 |
| JP | 57-84945 | 5/1982 |
| JP | 63-160898 | 7/1988 |
| JP | 3-29661 | 2/1991 |
| JP | 5-111526 | 5/1993 |
| JP | 6-511183 | 12/1994 |
| JP | 10-509606 | 9/1998 |
| WO | WO 96/13161 | 5/1996 |
| WO | WO 98/42295 | 10/1998 |

* cited by examiner

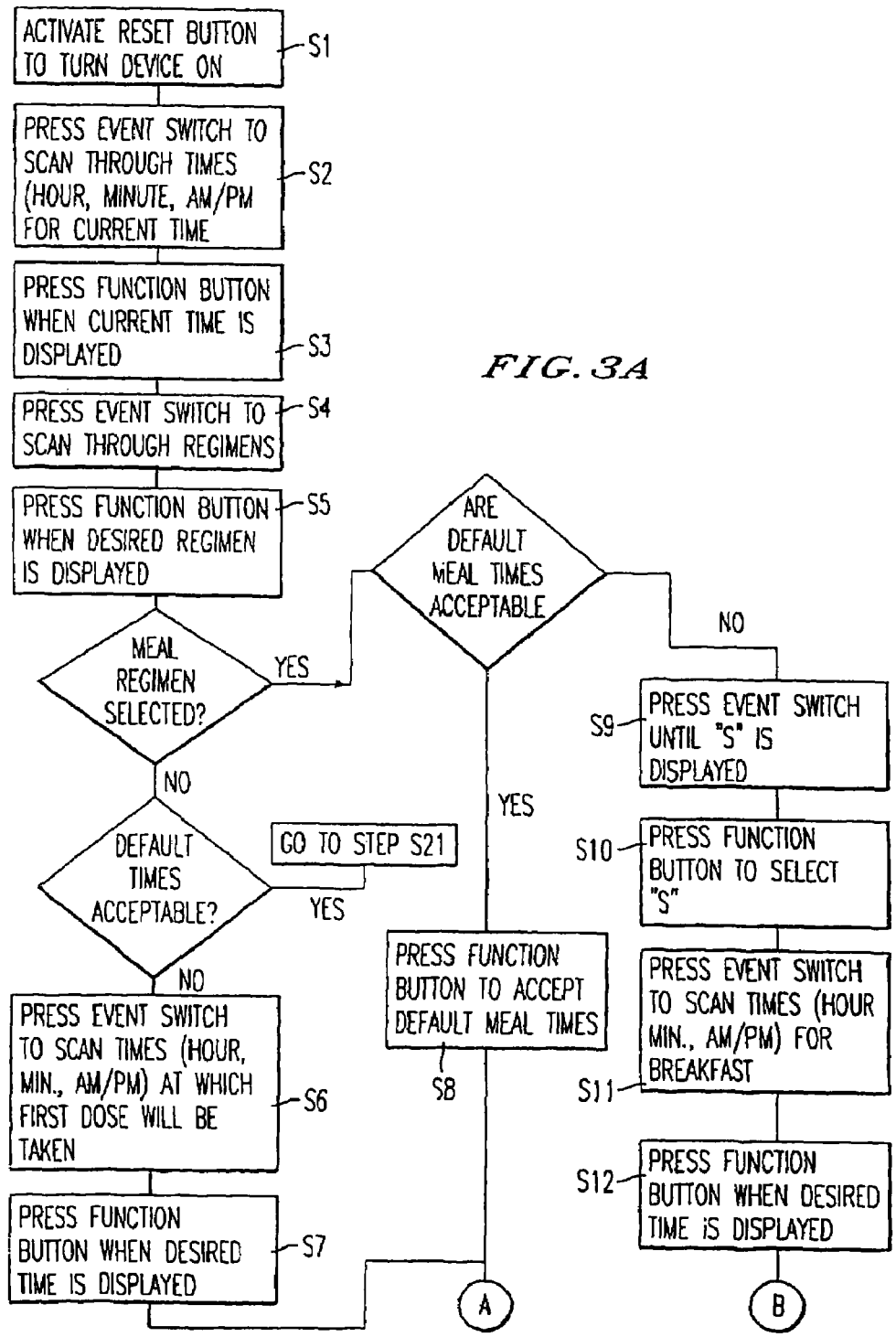

FIG. 4

| REGIMEN NO. | INTERVAL |
| --- | --- |
| 0 | EVERY 24 HRS. ; ONCE DAILY |
| 1 | B,D ⎫ |
| 2 | B,L,D ⎬ WITH MEALS |
| 3 | B,L,D,N ⎭ |
| 4 | EVERY 48 HRS. ; EVERY OTHER DAY |
| 5 | EVERY 6 HRS. ; 4 TIMES DAILY |
| 6 | EVERY 4 HRS. ; 6 TIMES DAILY |
| 7 | EVERY 8 HRS. ; 3 TIMES DAILY |
| 8 | EVERY 12 HRS. ; 2 TIMES DAILY |

B = BREAKFAST
L = LUNCH
D = DINNER
N = BEDTIME

FIG. 9

| REG# | PRESCRIBED REG. | DOSAGE TIME | RANGE |
|---|---|---|---|
| 0 | CUSTOM | UP TO 10 USERS SPECIFIED | USER SPECIFIED |
| 1 | QD. QAM.QPM. QHS. ONCE A DAY. ONCE EVERY 24 Hr | $1^{ST}$ | +/- 4 Hr |
| 2 | BID. TWICE A DAY | $1^{ST}$ AND $5^{TH}$ | +/- 3 Hr |
| 3 | TID. THREE TIMES A DAY | $1^{ST}$, $3^{RD}$, AND $6^{TH}$ | +/- 2 Hr |
| 4 | QID. FOUR TIMES A DAY | $1^{ST}$, $2^{ND}$, $4^{TH}$ AND $6^{TH}$ | +/- 1 Hr |
| 5 | QXXH. TAKE EVERY Hr | INTERVALS CALCULATED ON BASIS OF XX | +/- 0.25XX OR 4 Hr |
| 6 | PRN. XXHr. TAKE AS NEEDED EVERY XX HR | LAST DOSE (OR INITIAL DOSE) +XX | NONE |
| 7 | MONTH CYCLE | $1^{ST}$ ON SPECIFIED DAYS | +/- 4 Hr |
| 8 | WITH FOOD | DEFAULT OR SET | +/- 1 Hr |
| 9 | AFTER MEALS | DEFAULT OF SET TIMES +2 Hr | +/- 1 Hr |
| 10 | BEFORE MEALS | DEFAULT OR SET TIMES - 1 Hr | +/- 1 Hr |
| 11 | EMPTY STOMACH | SELECTED MEALTIMES + 2 Hr | -15 Min/+1 Hr |
| 12 | FIXED CYCLE | $1^{ST}$ ON DAYS ON/OFF | +/- 4 Hr |
| 13 | GO / STOP | START AND STOP DATES | |
| 14 | D OF WEEK | $1^{ST}$ ON SELECTED DAYS | +/- 4Hr |
| 15 | RECORD ONLY | | |

*Fig.26A*  [ENTER PRGM] —F4   [MED NAME —F5 / MED 10 —F7]

*Fig.26B*  [ENTER PRGM] —F4   [REGIMEN —F5 / 1/DAY —F7]

*Fig.27A*  [ENTER PRGM] —F4   [1st OF DAY —F5 / 08:00A —F7]

*Fig.27B*  [ENTER PRGM] —F4   [1st OF DAY —F5 / 08:00A]

*Fig.27C*  [PRGM] —F4   [EDIT SAVE / ACYCLOV —F7]

*Fig.27D*  [PRGM] —F4   [EDIT SAVE —F5 / ACYCLOV —F7]

*Fig.28*  [ENTER PRGM] —F4   [INTERVAL —F5 / 2 HR —F7]

PRESCRIPTION COMPLIANCE DEVICE AND METHOD OF USING DEVICE

CROSS-REFERENCES TO RELATED APPLICATIONS

This application is a Continuation Application of and is based upon and claims the benefit of priority under 35 U.S.C. § 119(e) from U.S. application Ser. No. 10/481,727 now U.S. Pat. No. 7,330,101, filed Sep. 3, 2004, which is a National Stage Application of International Application No. PCT/US02/19940, filed Jun. 24, 2001; which claims priority to U.S. Provisional Application Ser. No. 60/299,761 filed Jun. 22, 2001; the entire contents of which are herein incorporated by reference.

BACKGROUND OF THE INVENTION

1. Field of the Invention

This invention relates to an apparatus which aids patients in complying with instructions given by a physician for taking prescription medication, and more particularly, to a device which is programmable in accordance with the physician's instructions or desired regimen.

2. Discussion of the Background Art

A variety of devices have been proposed for recording intervals at which patients, especially those under the care of an attendant, take medication at periodic intervals prescribed by a physician. If the patient or his medical care provider ignores the proper instructions and repeats the dose too frequently or fails to administer or take medication at the proper time, the concentration of medication in the patient's body may become too high or too low. In order to ensure that medications are taken at the proper time, a variety of devices, such as the one disclosed in U.S. Pat. No. 4,361,408, have been devised to generate audible and/or visible prompting or alarm signals that remind a patient or his caretaker to administer the correct dosages at the correct time. Such devices have been complex and costly, inconvenient to program, and have not been flexible enough in establishing varying time intervals at which the medication needs to be administered.

SUMMARY OF THE INVENTION

Accordingly, one object of this invention is to provide a low cost, easy to use prescription compliance device that has the flexibility of operating in accordance with various different medication-taking intervals.

Another object of this invention is to provide a prescription compliance device which is easily programmable either by activating a programmer on the device itself or by remotely programming the device via a wireless link. Multiple programming regimens which correspond to different medication-taking intervals and medication-types may also be programmed into the device.

Yet another object of this invention is to provide a prescription compliance device which records the event of taking a dose of medication and displays the time at which the next dose of medication is to be taken.

A still further object of this invention is to provide a prescription compliance device having a timer which measures the time that has elapsed since the patient last took a dose of the medication and an alarm which is activated at times when the patient is to take the next dose of medication.

A further object of this invention is to provide a prescription compliance device that maintains a count of the number of doses remaining in a patient's prescription and displays the count so that a patient will know when to have the prescription refilled.

Another object of this invention is to provide a prescription compliance device that alerts a patient when the patient has missed a scheduled dose of medication or has taken a dose of medication at a non-scheduled time.

Yet another object of this invention is to provide a prescription compliance device which records the times at which a patient takes each dose of medication in a format that can be easily accessed.

Another object of the invention is to provide a prescription compliance device which aids in the management of a multitude of medications.

These and other objects are accomplished by a prescription compliance device which includes a microcontroller, a program memory which stores data representing a plurality of pre-programmed medication-taking regimens for single and multiple medications, an oscillator which controls timing functions of the device, a selector selecting one of the regimens and programming the device in accordance with the selected regimen, a display which alternately displays the current time, the time at which a next dose of medication is to be taken in accordance with the regimen selected by the selector, and the number of doses remaining in a prescription, and an alarm which alerts the patient at times when the patient is scheduled to take a dose of medication. The device may also include a memory which records the times at which a patient takes each dose of medication in a format that can be easily accessed.

The selector includes an event switch which is activated by the patient after taking a dose of medication to record the taking of the medication, the event switch causing the microcontroller to effect the display of the next time at which a dose of the medication is scheduled to be taken, in accordance with the regimen selected by the selector.

The event switch and a function button are provided for programming the regimens by which the medication is to be taken, the day of the week on which the first dose is to be taken, the time at which the first dose is to be taken or the designation of meals during which the first dose is to be taken, and the number of doses in a patient's prescription.

Programming may be done either directly by using the function button and the event switch or remotely via a wireless link. To program from a remote location, the device is provided with a wireless transmitter/receiver and an external wireless transmitter/receiver configured to be connected to an input device. The external wireless transmitter/receiver communicates with the wireless transmitter/receiver via a wireless link to select one of the regimens and to program the device in accordance with the selected regimen.

The display includes a first display area which alternately displays the alerts, alarms and notifications, menu selections and other information, a second display area which alternately displays the name of the medication the name of the regimen or other information, a third display area which alternately displays the day of the week and time in addition to other information, a fourth display area which provides special alert message in addition to other information. Further, for each of the above listed display areas, other information may include the calendar date, the patient name, the patient phone number, and icon indicating the nature of the information currently displayed in the other display areas, AM, PM designations, historical data stored in the device memory, codes describing displayed information, advise on how medications is to be taken, etc.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 3A-3E are flow diagrams illustrating the steps followed when operating the prescription compliance device;

FIG. 4 is a table listing examples of common medication-taking regimens which may be programmed into the prescription compliance device;

FIG. 9 is another table listing examples of common medication-taken regimens which may be programmed into the prescription compliance device;

FIGS. 26A-31D illustrate an operation for programming regimens;

DESCRIPTION OF THE PREFERRED EMBODIMENTS

Figure 1:
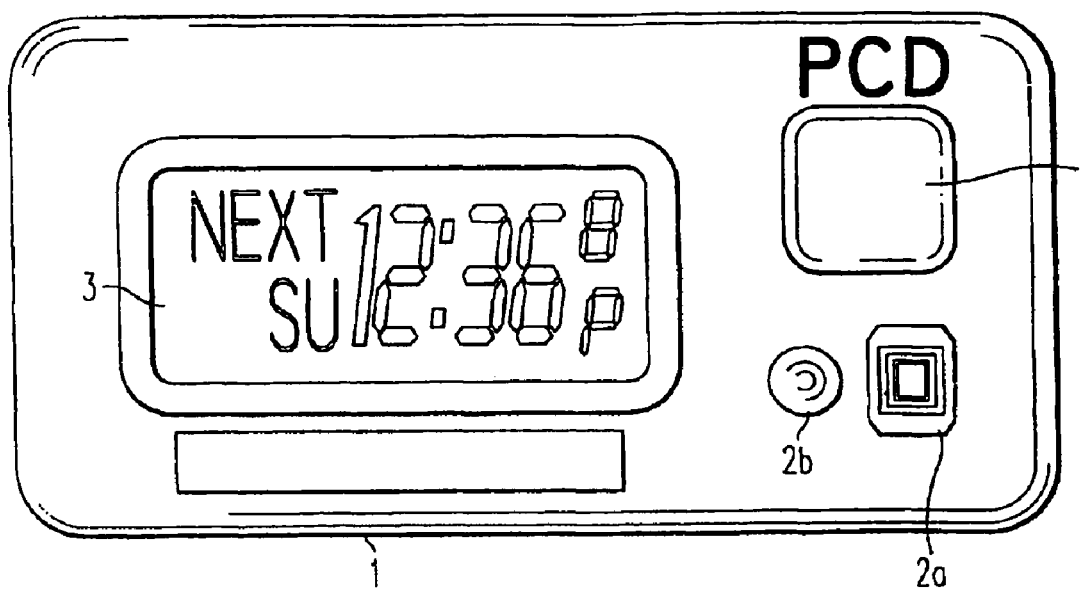
FIG. 1 is an illustration of a prescription compliance device in accordance with a first embodiment of the present invention.

Referring now to the drawings, wherein like reference numerals designate identical or corresponding parts throughout the several views, and more particularly to FIG. 1 thereof, a prescription compliance device 1 according to a first embodiment of the present invention includes a function button 2a, a reset button 2b, and an event switch 4 for programming the device, and a display 3 for displaying the programmed information. The event switch 4 is activated by the patient upon the taking of a dose of medication. Note, the reset button 2b is shown for clarity purposes as being on the front surface of the device. However, the reset button 2b is preferably on the back surface of the device to avoid accidentally resetting the device.

Prescription Compliance Device for Single Medications

Figure 2:
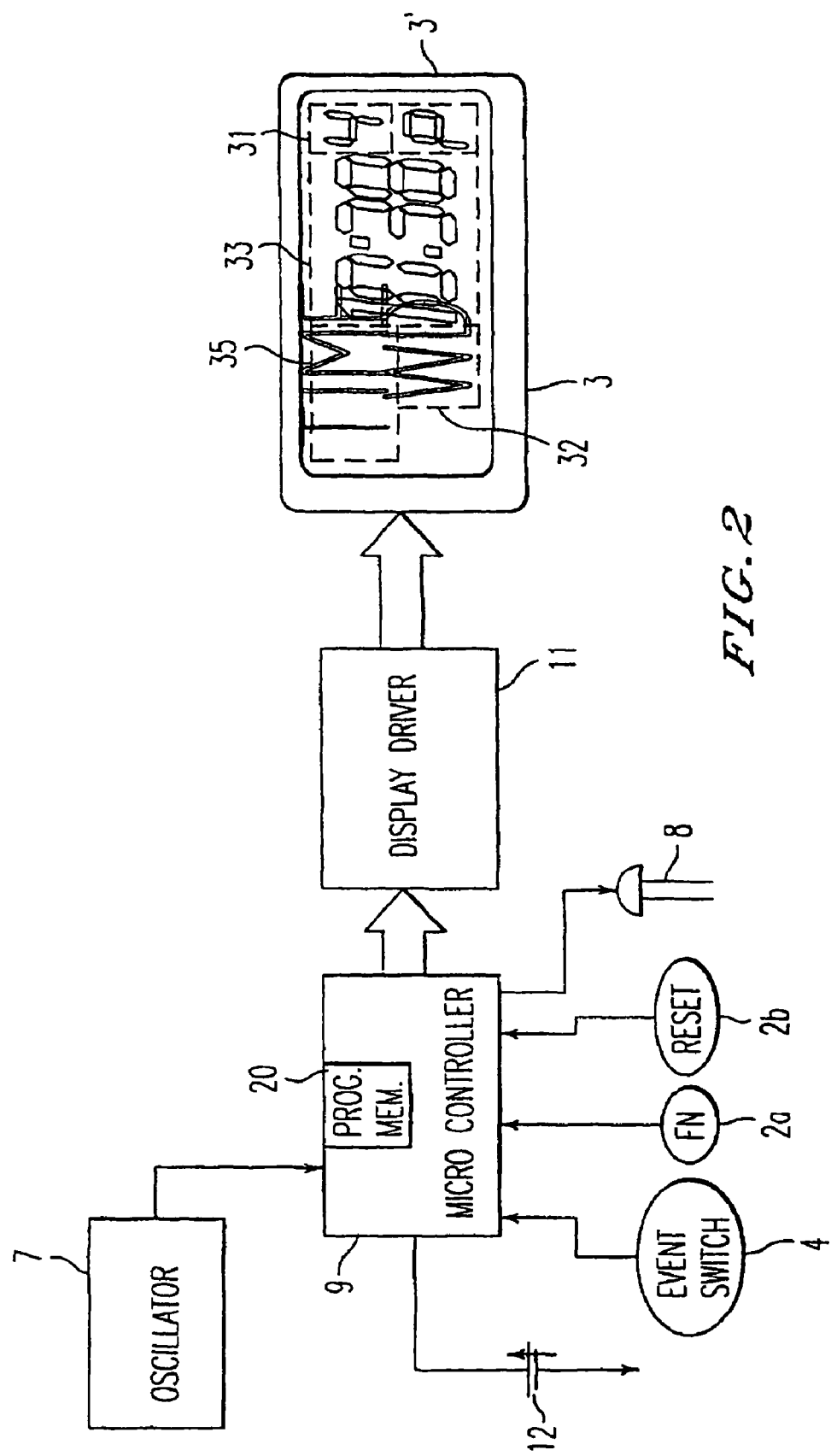
FIG. 2 is a block diagram of a prescription compliance device of FIG. 1.
Figure 3B:
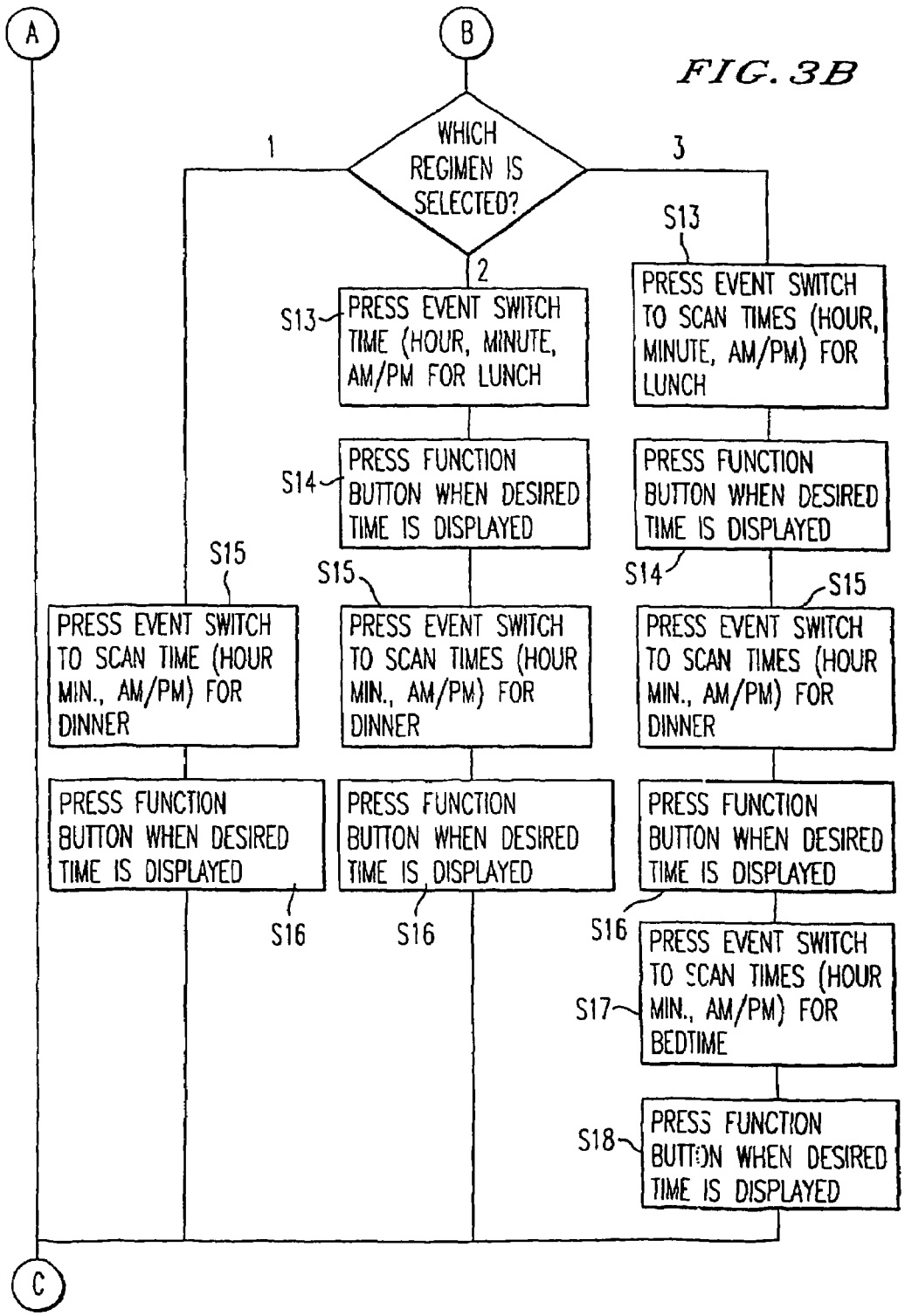
Figure 3C:
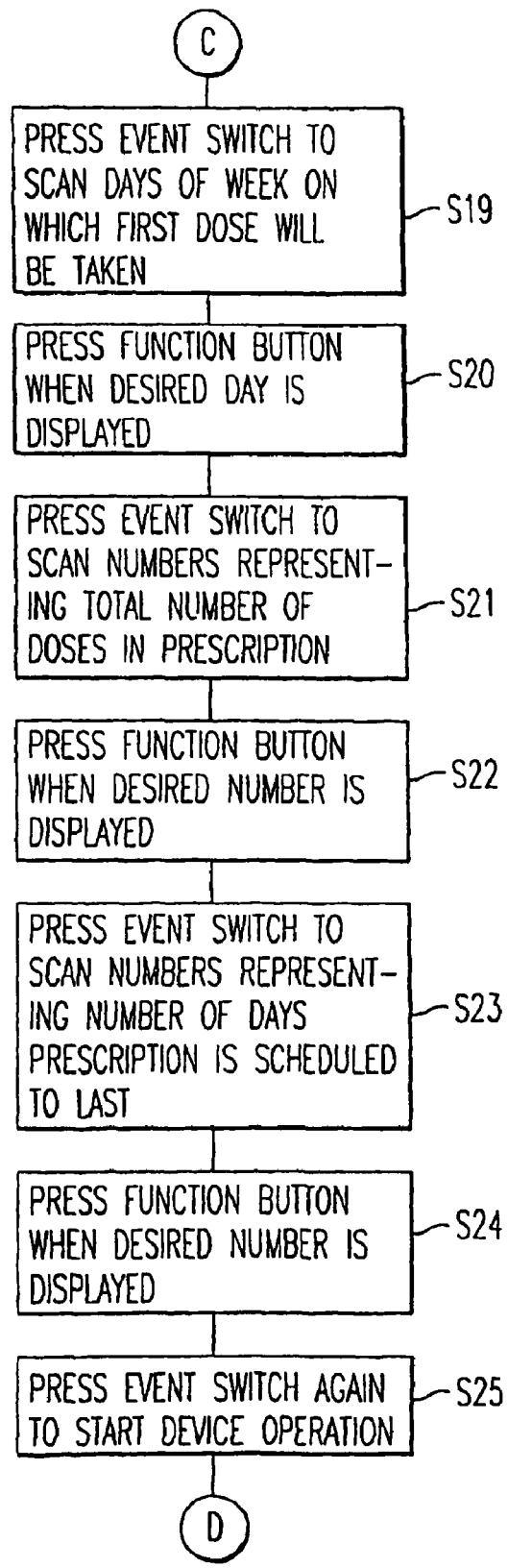
Figure 3D:
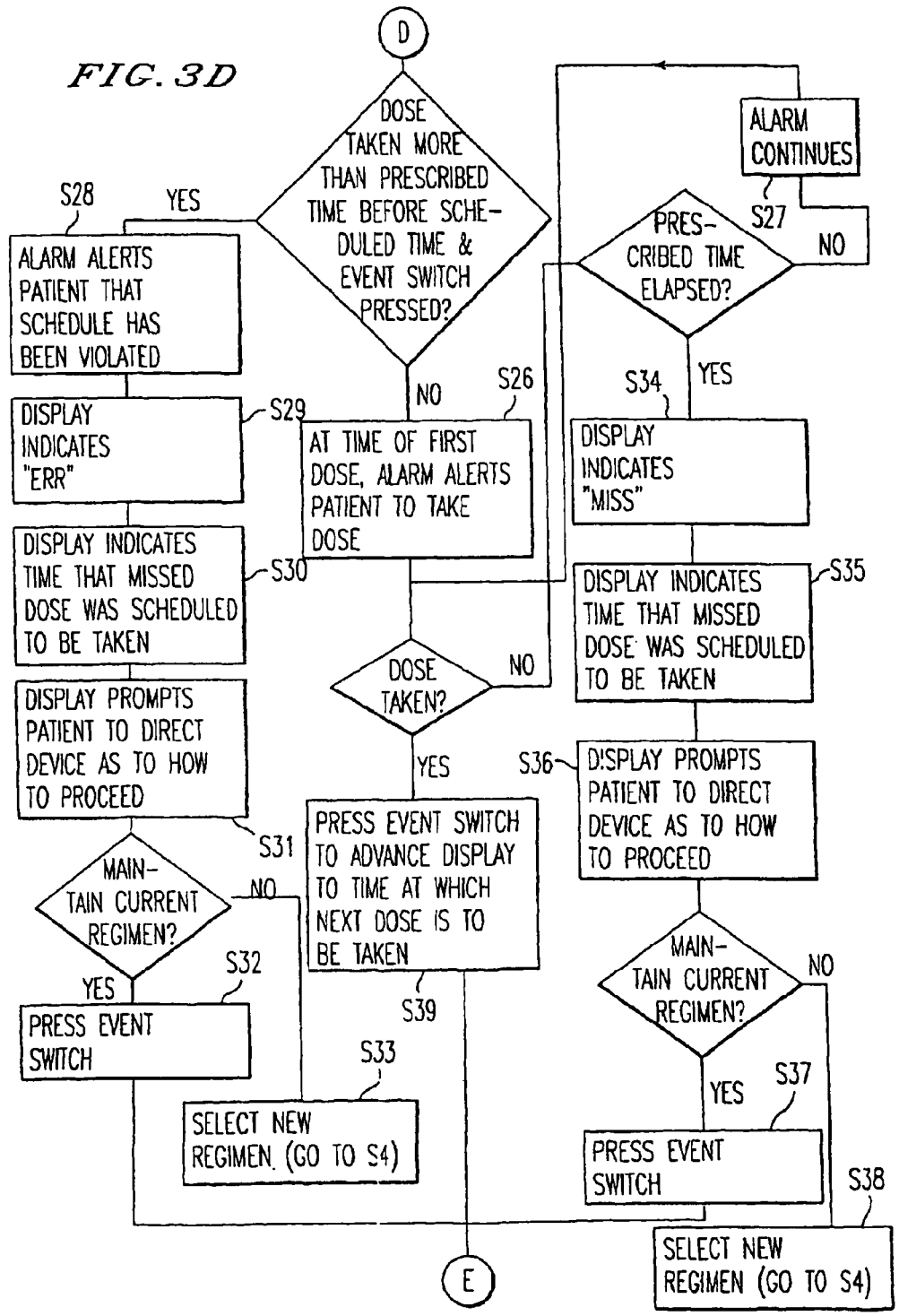
Figure 3E:
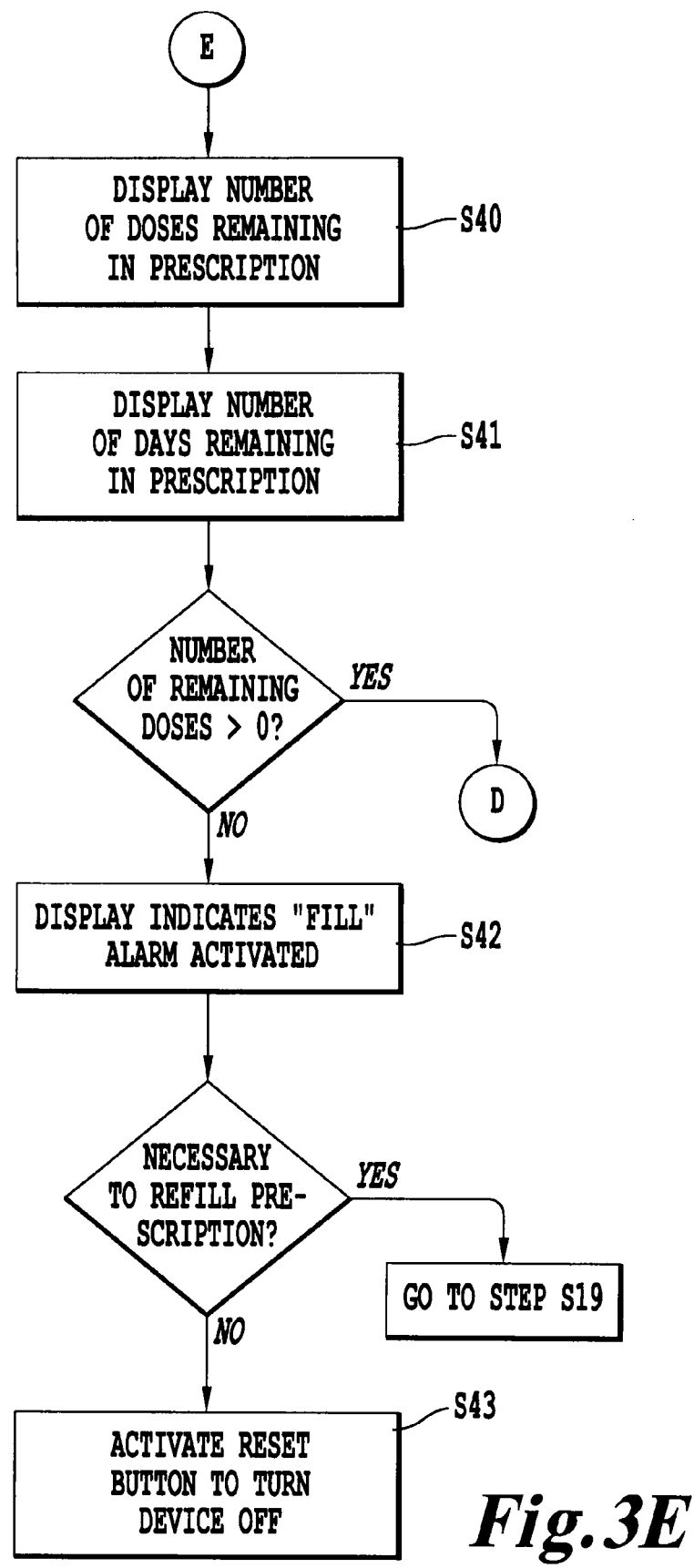

FIG. 2 illustrates a block diagram of the prescription compliance device according to the first embodiment of the invention. The illustrated and described configuration is exemplary and any desired hardware implementation can be used. An 8-bit microcontroller 9 such as (Microchip Part No. PIC 16C954, for example) which controls the overall functions of the device includes a program memory 20 for storing preprogrammed medication-taking regimens. A 32 KHz crystal oscillator 7 controls all timings of the device. The program memory 20 is preferably a dedicated chip mask read only memory (ROM), although other nonvolatile memories such as a flash memory or EEPROM may be used. The specific parameters of the microcontroller, program memory, and the oscillator are set forth here solely for illustrative purposes and are not intended to limit the scope of the invention. The use of equivalent elements is contemplated within the scope of this invention.

The microcontroller receives inputs from the function and reset buttons 2a, 2b and from the event switch 4 and controls the device functions in accordance with the pre-programmed regimens stored in program memory 20. The microcontroller 9 is connected via an 8-bit bus 21 to display driver 11 which drives the display 3 to display relevant information in display areas 31-35. The display 3 is preferably a liquid crystal display (LCD) and the display driver 11 an ASIC LCD driver. Battery 12 is preferably a 3 volt battery and alarm circuit 8 may visually and/or audibly prompt the patient to take medication. However, equivalents are also within the scope of the invention.

The operation of the prescription compliance device according to this embodiment of this invention will now be described with reference to FIGS. 3A-3E. Patients who are under the care of an attendant are instructed to take medication at periodic intervals as prescribed by a physician. Upon receiving the prescription, the patient or his medical care provider employs the prescription compliance device to aid the patient in complying with the instructions given by the physician.

First, the device must be switched from an OFF state to an ON state by pressing the reset button (Step S1). A "SET" icon is displayed in display area 35 to indicate that the device is in a setup mode. The patient first sets the current time (Steps S2 and S3) as follows.

The event switch 4 is pressed and the microcontroller 9 directs the display area 33 to blink hour digits "12". Hours "1" through "12" are scanned through by pressing the event switch 4 and the appropriate hour is selected by pressing the function button 2a when that hour is displayed.

The minutes tenth digit then blinks "0" and the digits "0" through "60" are scanned through by pressing the event switch 4. The appropriate digit is selected by pressing the function button 2a when that digit is displayed.

The minutes unit digit then blinks "0" and the digits "0" through "9", are scanned through by pressing the event switch 4. The appropriate digit is selected by pressing the function button 2a when that digit is displayed.

The display area 34 then blinks "A" and the patient selects AM or PM time designations using the event switch 4 to toggle between the two and the function button 2a to select. This completes the setting of the current time.

The patient now selects the regimen by which the prescription medication is to be taken. Upon depressing the event switch 4, the display area 35 displays "RGMN" and the display area 31 blinks "0", prompting the patient to scan through and select a desired regimen using the event switch 4 (Step S4). FIG. 4 lists examples of common programming regimens which may be pre-programmed into program memory 20. These regimens are listed only by way of example and other regimens are possible.

In FIG. 4, regimens are provided for taking the medication 1, 2, 3, 4, or 6 times daily, taking the medication with breakfast and dinner, with breakfast, lunch, and dinner, or with breakfast, lunch, dinner, and at bedtime, and for taking the medication once every 48 hours.

The patient presses the event switch 4 to advance through the programming regimens. During scanning, regimen numbers appear in display area 31 and descriptions of the regimens appear in display area 35 so that the patient knows which regimen each number corresponds to. For example, when "8" appears in display area 31, "3:D" appears in display area 35 to indicate to the patient that programming regimen 8 corresponds to taking medication three times daily.

When the desired regimen is displayed, the function key 2a is pressed (Step S5) and the display 3 prompts the patient to choose between standard, pre-programmed default times corresponding to the selected regimen or setting a specific time at which the first dose is to be taken. If the default times for taking the medication are acceptable, the patient presses the event switch 4 and is then prompted to enter the number of doses in the prescription (Step S21).

If the patient instead wants to set the time at which the first dose is to be taken, the microcontroller 9 directs the display area 33 to blink hour digits "12". Unless the patient selects one of the meal regimens, the time of day at which the first dose of the medication is to be taken is next programmed (Steps S6 and S7). Hours "1" through "12" are scanned through by pressing the event switch 4 and the appropriate hour is selected by pressing the function button 2a when that hour is displayed.

The minutes tenth digit then blinks "0" and the digits "0" through "60" are scanned through by pressing the event switch 4. The appropriate digit is selected by pressing the function button 2a when that digit is displayed.

The minutes unit digit then blinks "0" and the digits "0" through "9" are scanned through by pressing the event switch 4. The appropriate digit is selected by pressing the function button 2a when that digit is displayed.

The display area 34 then blinks "A" and the patient selects AM or PM time designations using the event switch 4 to toggle between the two and the function button 2a to select. This completes the setting of the time at which a first dose of medication is to be taken by the patient.

If one of the meal regimens is selected, the medication is to be taken with meals the times of which will vary from person to person. The program memory 20 has pre-programmed therein standard meal times (breakfast, lunch, dinner) during which most persons normally eat. However, the device is flexible enough to allow for different meal times, as will now be explained.

After a meal regimen is selected, display area 33 blinks "D" for default meal times. If the patient eats meals at the standard times programmed into the program memory 20, then the function button 2a is pressed when "D" is displayed (Step S8). If the patient eats at different times, then pressing the event switch 4 (Step S9) allows the patient to toggle between "D" and "S" (indicating 'set'). Pressing the function key 2a when "S" is displayed (Step S10) allows the user to set his breakfast, lunch, dinner, and bedtimes as follows. After the function key 2a is pressed, "BRKF" appears in display area 35 and "12" blinks in display area 33. The patient's breakfast time (hour, minute, AM/PM) is entered as described above (Steps S11 and S12).

After programming the breakfast time, the operation varies according to the specific regimen selected. For explanatory purposes, regimens 1, 2, and 3 refer to the meal designations listed in FIG. 4. If regimen 2 or 3 has been selected, "LNCH" appears in display area 35 and the time setting process is repeated to set the patient's lunch time (Steps S13 and S14). "DINR" then appears in display area 35 under regimens 1, 2, and 3 and the patient's dinner time is similarly set (Steps S15 and S16). Finally, "BDTM" appears in display area 35 if regimen 3 is selected and the patient's bedtime is set as described above (Steps S17 and S18).

Once the time/meal designations have been programmed, the display area 32 then blinks "SU", prompting the patient to program the day of the week on which the first dose is to be taken. The days "SU" through "SA" are scanned through by pressing the event switch 4 (Step S19) and the appropriate day is selected by pressing the function button 2a (Step S20).

The display area 35 then displays "CNT," prompting the patient to enter the number of doses in the current prescription. Display area 33 blinks "0" and the patient scans up using the event switch 4 until the desired number is displayed (Step S21). The function button 2a is then pressed to select this number (Step S22).

The display area 35 then prompts the patient to enter the number of days that the current prescription is scheduled to last. Display area 33 blinks "0" and the patient can scan up using the event switch 4 until the desired number is displayed (Step S23). The function button 2a is then pressed to select this number (Step S24).

This completes the setup process. Display area 35 next displays "STRT" and display area 33 displays a question mark ("?"). When the user presses the event switch 4, the device is in an operation mode (Step S25). The operation mode is defined a mode the device resides in after the user has programmed the desired options. Display 3 may alternately display the current time or the time at which the next dose is to be taken. When the current time is displayed, display area 35 displays "TIME," display area 31 displays the number of the regimen selected by the patient, display areas 33 and 34 display the current time of day, and display area 32 displays the current day of the week. When the time of taking the next dose of medication is displayed, display areas 33 and 34 display the time at which the next dose is to be taken, display area 32 displays the day of the week on which the next dose is to be taken, display area 31 continues to display the number of the selected regimen, and display area 35 displays "NEXT."

After the device is programmed and the event switch 4 is pressed to enter the operation mode, the patient is aware of the day and time at which the first dose of the medication must be taken. At the time for taking the first dose, the microcontroller 9 directs the alarm circuit 8 to emit an audible and/or visible signal to alert the patient that the first dose must be taken at this time (Step S26). The alerting signal continues to be emitted intermittently until the patient takes the dose and presses the event switch 4 or until a prescribed time has elapsed (Step S27). During this time, display area 35 displays "TAKE" indicating that it is time to take the next dose. If the patient takes the dose more than a prescribed time before the scheduled time and presses the event switch 4, the alarm circuit 8 is activated (Step S28) and the display area 35 indicates "ERR" (Step S29) to indicate that the patient has not properly followed the selected regimen.

If the patient fails to take the dose within a prescribed time after the scheduled time while the alarm circuit 8 is activated, display area 35 displays "MISS" (Step S34) indicating that the patient has missed taking the scheduled dose. The display then indicates the time that the missed dose was scheduled to be taken (Step S35) and prompts the patient to direct the device as to how to proceed (Step S36). At this point the patient may press the event switch 4 to maintain the current regimen (Step 37) or may select a new regimen (Step S38).

Upon taking the first dose, the patient presses the event switch 4 which records the taking of the medication and causes the microcontroller to automatically calculate the time/meal at which the next dose of medication must be taken according to the selected regimen and to effect the display of this time on the display 3 (Step S39). The microcontroller also subtracts the dose taken from the total number of doses in the prescription to update the count of remaining doses. This number is displayed in display area 33 while "LEFT" is displayed in display area 35 to indicate the number of doses remaining (Step S40).

Likewise, at the end of each day the microcontroller subtracts one from the total number of days in the prescription to update the count of remaining days. This number is displayed in display area 33 to indicate the number of days remaining (Step S41).

These operating procedures are repeated for as long as the patient's prescription is valid. When the number of doses in the prescription has been nearly exhausted (i.e., six doses or less remaining), the display indicates "FILL" and the alarm circuit is activated (Step S42). If the patient has the prescription refilled at the direction of a physician, the operating procedures are resumed at Step S21. Otherwise, if the patient has completed his prescription and needs no further medication, the device is turned off by pressing the reset button 2b (Step S43).

Prescription Compliance Device for Multiple Medications

Figure 5:
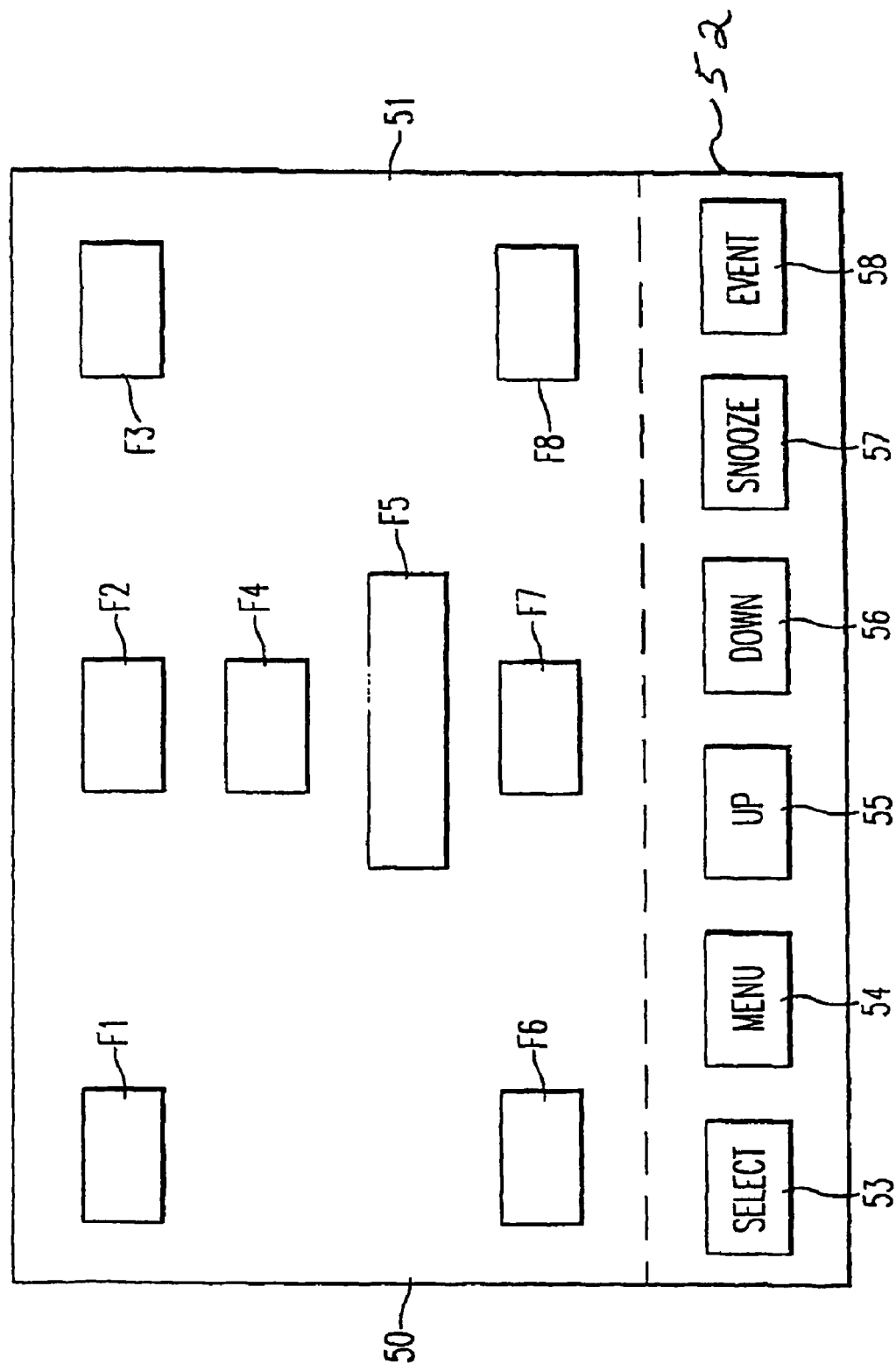
FIG. 5 is an illustration of a prescription compliance device in accordance with a second embodiment of the present invention.

FIG. 5 illustrates a block diagram prescription compliance device according to a second embodiment of the invention. In this embodiment, the user may program the device and monitor the status of multiple medications.

In addition to the central processor and supporting circuitry shown in FIG. 2 for the first embodiment, the device 50 according to the second embodiment includes a display 51 and a key pad 52. The display 51 includes eight character and/or graphical display fields F1-F8 which display information to the user. This information could also be presented using a dot matrix display and/or a scrolling display. Exemplary manners of implementing the display include using a liquid crystal display (LCD), a cathode ray tube (CRT), or a plasma display.

Referring to FIG. 5, the field F1 informs the user if multiple medications are to be taken, F2 informs the user of the specific prescription regimen being used with the medicine identified in F6 and F7, and F3 informs the user as to the status of the alarm or vibrator. When the device 50 is in an "OPERATE" mode, F4 informs the user whether or not to take a medication. If the user is to take a medication, F4 displays the word "TAKE," otherwise F4 displays the word "NEXT." An "OPERATE" mode is defined as a mode in which the device normally resides without an action on the part of the user. During a menu scan operation, the field F4 informs the user of the various options available. The field F4 also provides other information necessary to inform user of the nature or status of information that is being provided in the other fields. The field F5 displays time information, such as the day of the week, hour, minute, and AM or PM, and F6 is an optional character field identifying a memory slot relating to a specific medication F7 displays user programmed information identifying a specific medication and F8 advises the user if a program for a particular medication is operative or if it has been suspended.

As shown in FIG. 5, the device 50 also includes a keypad 52 with six keys: SELECT 53, MENU 54, UP 55, DOWN 56, SNOOZE 57 and EVENT 58. Other keys such as a numeric keypad, an alpha-numeric key pad, or a computer keyboard may be utilized, if desired. These keys are used during programming and operation of the device. The UP 55 and DOWN 56 keys allow the user to scroll through the options under the various menu items and the SELECT 53 key is used to select a desired option. Failure to activate the SELECT 53 key within a prescribed time interval returns the device to the OPERATE mode. Successive activation of the MENU 54 key causes the field F4 to display the menu choices shown in FIG. 6A. Pressing the SELECT 53 key while one of these options is displayed sets the device into the specific operation mode selected. The keypad 52 may be combined with the display 51, as illustrated in FIG. 5, or alternatively the keypad 52 may be separate from the display 51.

The multi-medicine prescription compliance device also includes a SNOOZE switch 57 and an EVENT switch 58. For the medication that is displayed in the fields F6 and F7, pressing the EVENT switch 58 causes the following events to occur. When the field F4 displays the word TAKE, the current date, time, and medication name is recorded, thus signifying the medication was taken. Then the field F4 displays the word NEXT and the next time to take the medication is displayed in the field F5. However, if other medications have earlier take times, the field F4 displays the appropriate NEXT or TAKE screen for that medication. When the field F4 displays the word NEXT and the time to take the medication is within a predetermined time range, the same sequence applies as when the F4 displays the word TAKE. However, when the field F4 displays the word NEXT and the time to take the medication has exceeded the predetermined time range, the current clock time and day are identified with the medication and the event is recorded. If the user fails to take the medication within the predetermined time range, the device advances to the appropriate next take time for that medication. In addition, the SNOOZE button 57 is used to silence the alarm. The alarm will then skip one interval before alerting the user again.

Figure 6A:
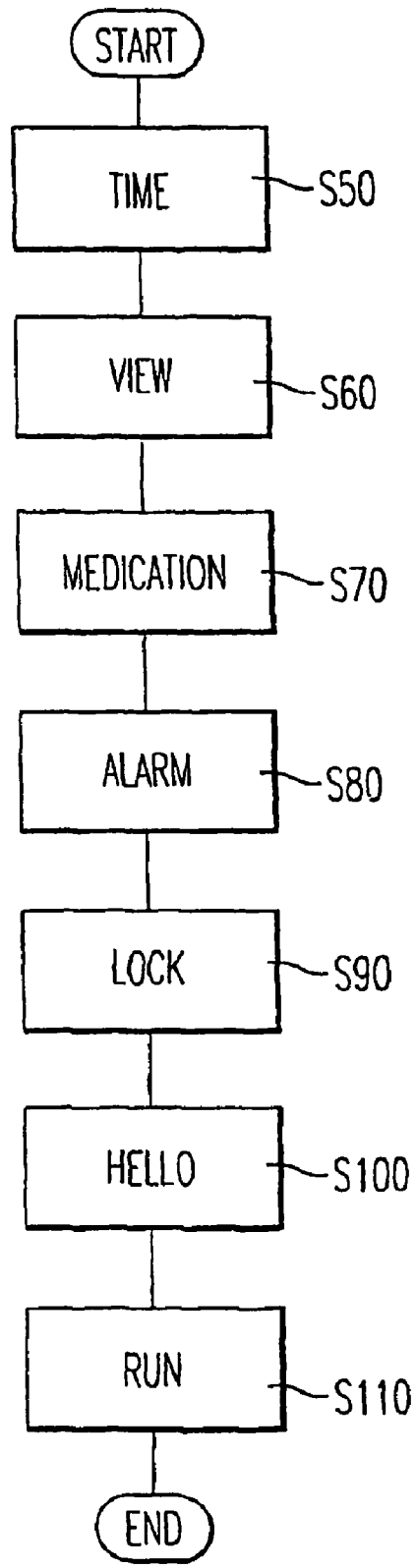
FIG. 6A is a flow diagram illustrating the menu choices available to the user.

The operation of the prescription compliance device according to the second embodiment of this invention will now be described with reference to FIGS. 6A-6H. FIG. 6A illustrates the choices available to the user which can be scrolled through by pressing the MENU 54 key.

The menu choices shown in FIG. 6A include the options of TIME (Step S50), VIEW (Step S60), MEDICATION (Step S70), ALARM (Step S80), LOCK (Step S90), HELLO (Step S100) and RUN (Step S110) which are explained below with respect to FIGS. 6B to 6H. The user scrolls through the options by pressing the MENU 54 key and then selects the desired option with the SELECT 53 key.

Figure 6B:
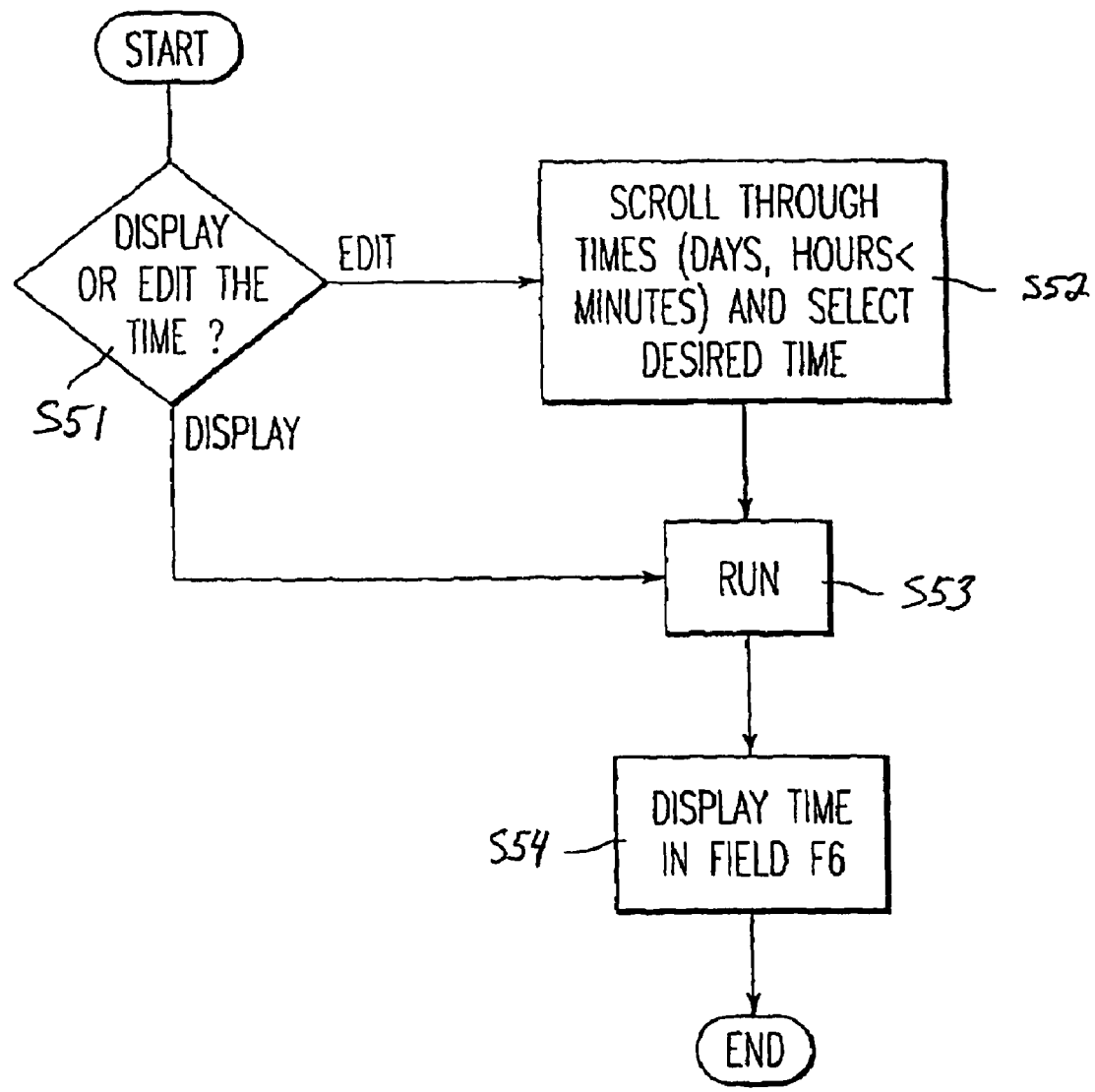
FIGS. 6B-6H are flow diagrams illustrating the steps followed when operating the menu options shown in FIG. 6A.

FIG. 6B illustrates the programming steps required to display or edit the current time. After the TIME option is selected (Step S50) in FIG. 6A, the user has a choice to display the current time or edit the current time (Step S51). If the user chooses to display the current time in Step S51 and executes the RUN option (Step S53), the current time will be displayed in the field F6 (Step S54) and the device returns to the OPERATE mode. If the user chooses to edit the current time in Step S51, the user scrolls through the times (days, hours, minutes) and selects a desired time (Step S52). After executing the RUN option (Step S53), the edited time will be displayed in the filed F6 and the device returns to the OPERATE mode.

Figure 6C:
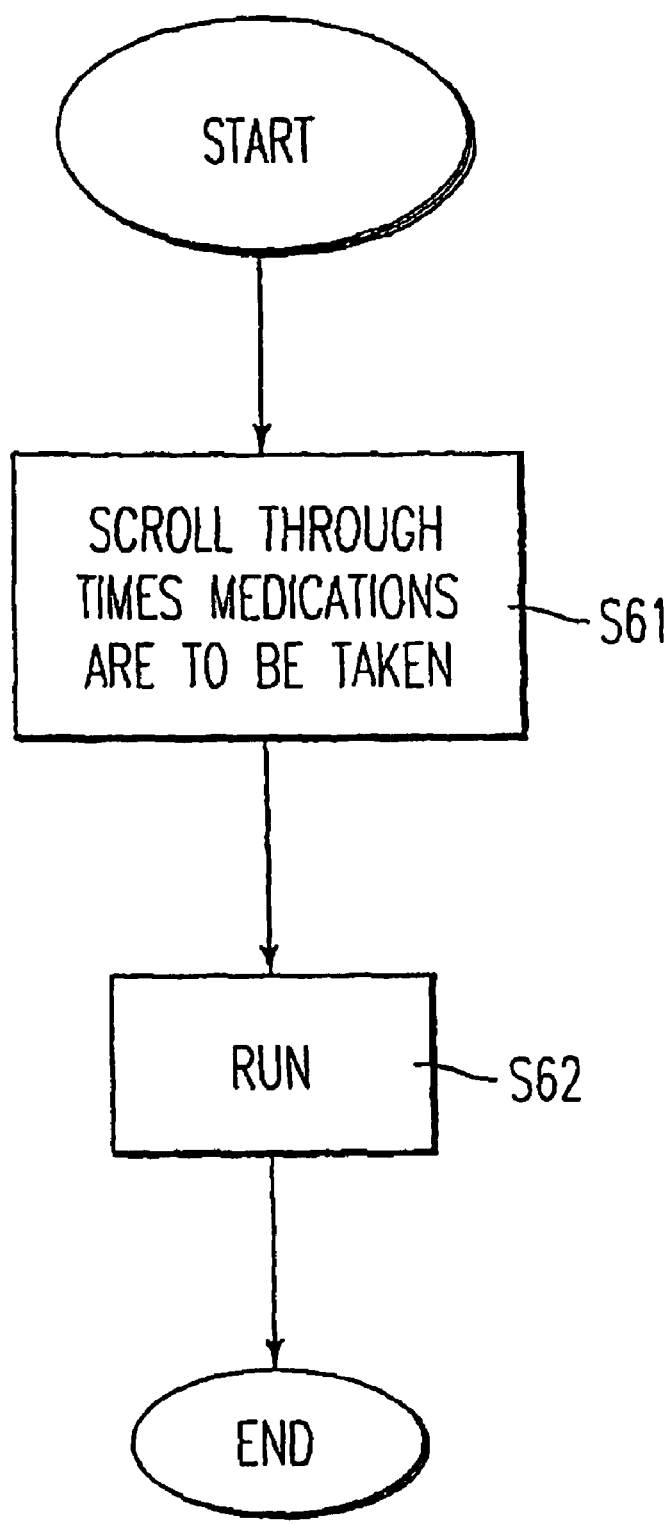

FIG. 6C illustrates the programming steps to view the different medications programmed into the device. After the VIEW option is selected (Step S60) in FIG. 6A, the user scrolls through the times that various medications are to be taken (Step S61). The time the medication is to be taken is displayed in the field F5 and the medicine identifiers are displayed in the fields F6 and F7. The user then selects the RUN option (Step S62) to return the device to the OPERATE mode.

Figure 6D:
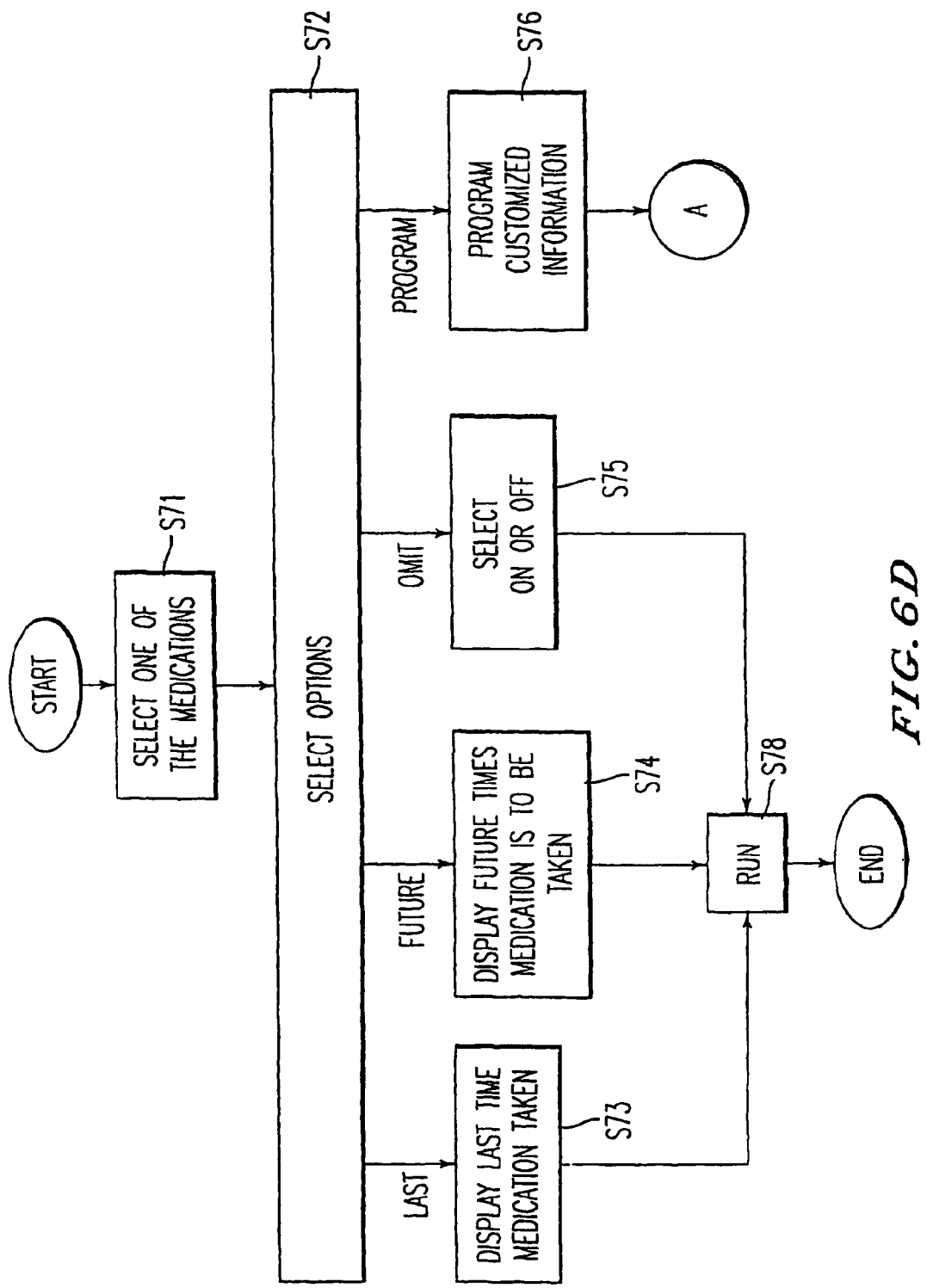
Figure 6E:
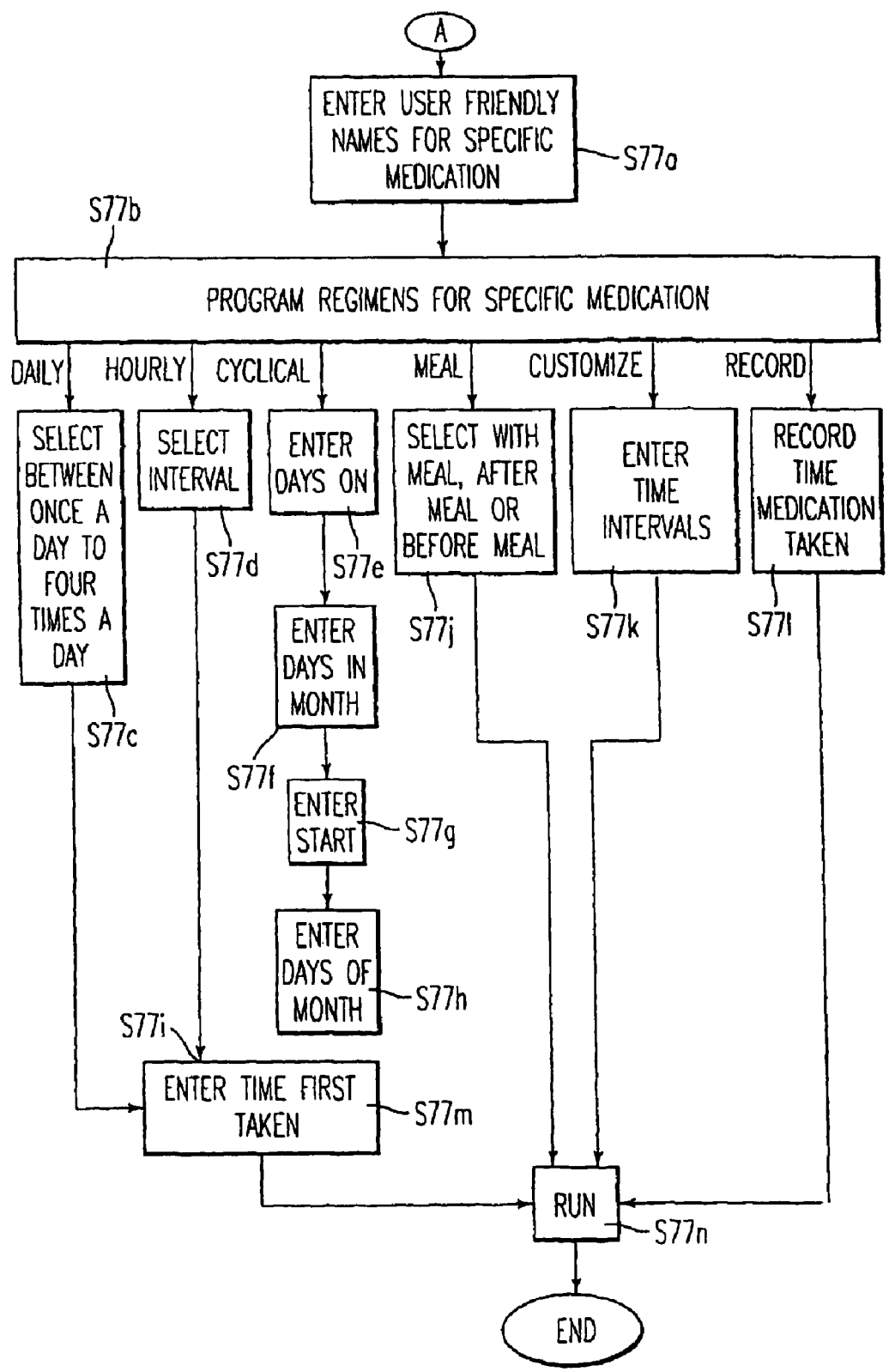

FIG. 6D illustrates the programming steps to view, omit or customize a specific medication. After the MEDICATION option is selected (Step S70) in FIG. 6A, the user scrolls through and selects one of the various medications (Step S71). Upon selecting a medication, the user scrolls through and selects an option (Step S72) including "LAST", "FUTURE", "OMIT" and "PROGRAM". The "LAST" option (Step S73) informs the user the last time the medication was taken. The "FUTURE" option (Step S74) allows the user to scroll through the future times the medication is to be taken and the "OMIT" option (Step S75) allows a user to temporarily turn off the program for the selected medication. The ON/OFF status for the medication is displayed in the field F8. The PROGRAM option (Step S76) allows the user to set (customize) program parameters for the selected medication. FIG. 6E illustrates the programming steps required to set the program parameters.

After the PROGRAM option is selected (Step S76) in FIG. 6D, the user enters customized information identifying the selected medication (Step S77a) in FIG. 6E. The customized information is displayed in the field F7. After Step S77a is performed, the user selects among several regimen options including a daily regimen (i.e., 1/Daily—once per day; 2/Daily—twice a day; 3/Daily—three times a day; and 4/Daily—four times a day) (Step S77c), and an hourly regimen in which the user selects hourly intervals to take the medication (Step 77d). Also included are a CYCLICAL (monthly cycle), MEAL (meal time), CUSTOMIZE (customized time intervals), and RECORD (record time at which medication was taken) regimens. Upon selecting the CYCLICAL option, the user enters the number of days in the cycle they take the medication (Step S77e). Then, the user enters the days in the month (Step 77f), the start date in the month that the user wants to start taking medication (Step 77g), and the current date of the month (Step S77h). The user also enters the time the first dose is to be taken (Step 77m) for the DAILY, HOURLY, and CYCLICAL regimens. After selecting the MEAL option, the user has a choice to take the medication WITH, AFTER or BEFORE meals (Step S77j). After selecting the CUSTOMIZE option, the user enters a specific time interval (Step S77k). The RECORD option (Step S77l) records the time the medication is taken. The user selects the RUN option (Step S77n) to return the device to the normal operating mode.

Figure 6F:
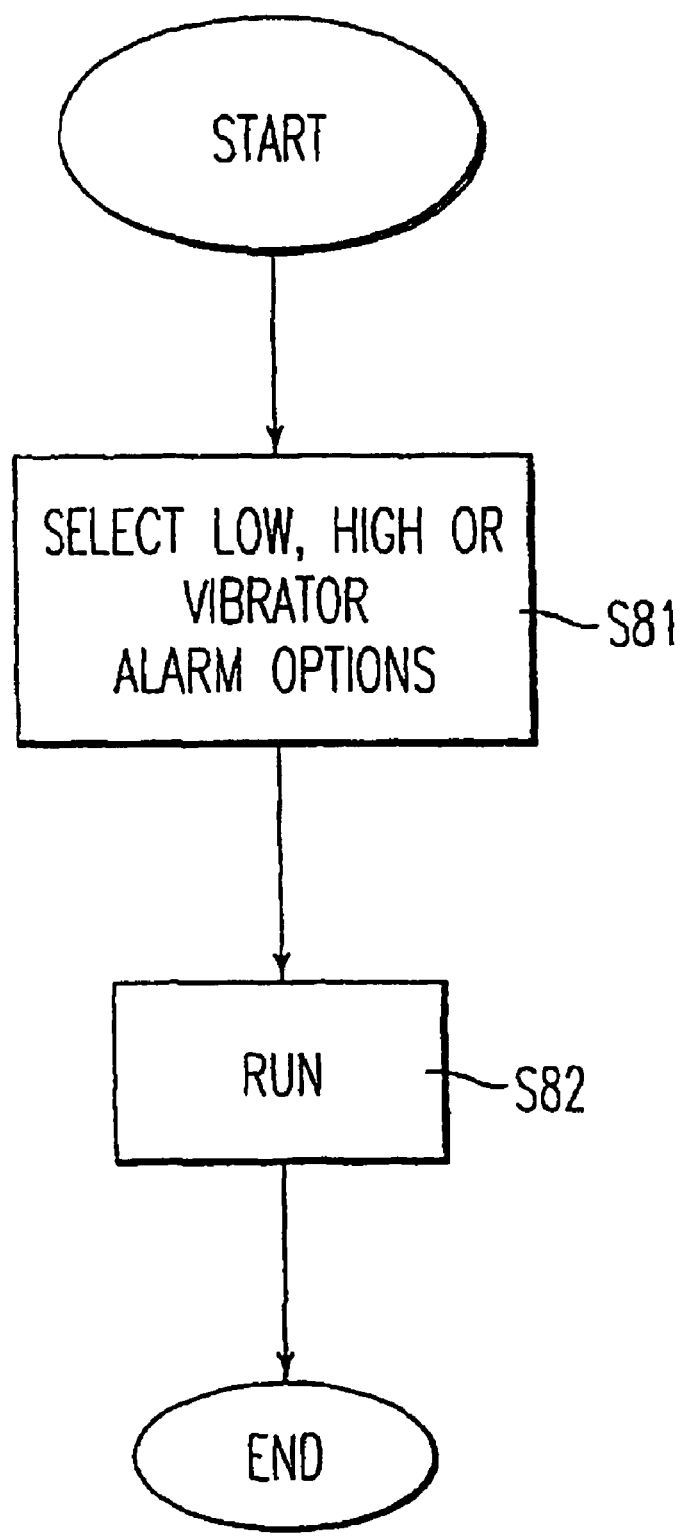

FIG. 6F illustrates the programming steps to program the ALARM options. After the ALARM option (Step S80) is selected in FIG. 6A, the user selects a low, high or vibrator ALARM (Step S81). The user then selects the RUN option (Step S82) to return the device to the normal operating mode.

Figure 6G:
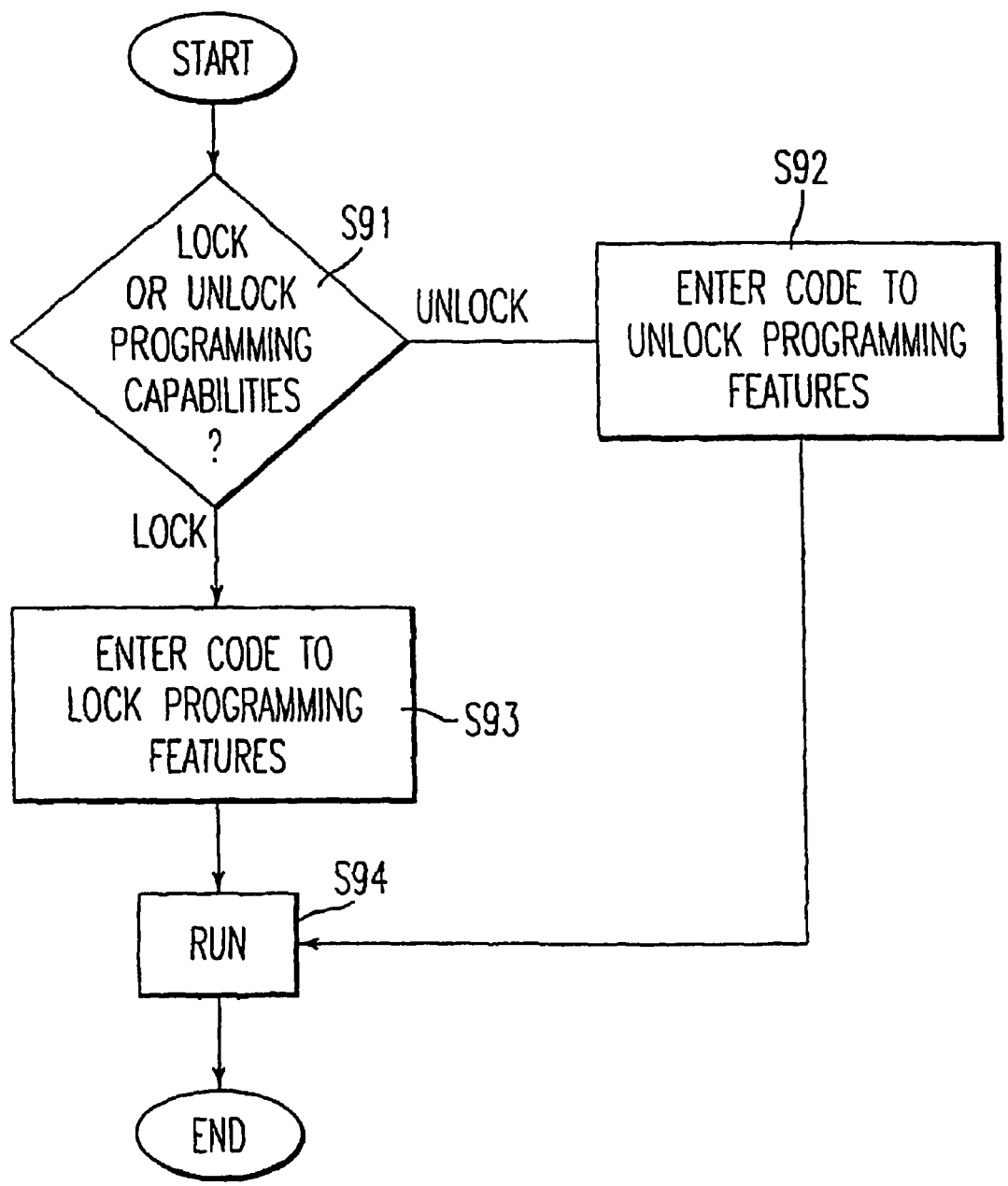

FIG. 6G illustrates the programming steps required to program the LOCK option. After the LOCK option (Step S90) is selected in FIG. 6A, the user has the choice to lock or unlock the programming features of the device (Step S91). If the user wants to lock the programming features, the user enters a code in Step S93. The code may include any combination of numeric or character values. If the user chooses to unlock the programming features, the user enters the code to unlock the device (Step S92). The user then selects the RUN option (Step S94) to return to the device to the OPERATE mode.

Figure 6H:
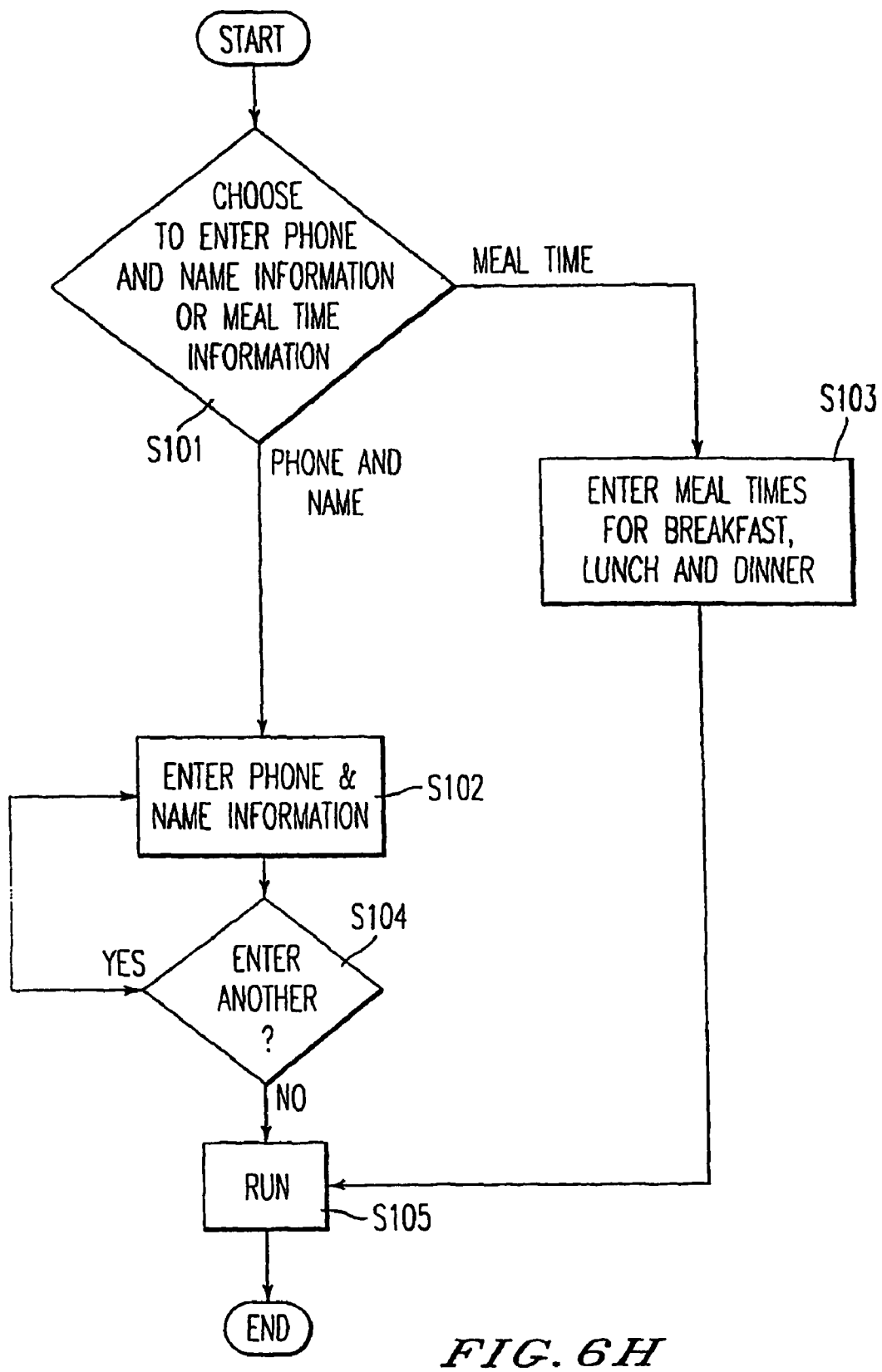

FIG. 6H illustrates the programming steps required to program the HELLO option. After the HELLO option is selected (S100) in FIG. 6A, the user may enter phone and name information or meal time information (Step S101). If the user chooses to enter phone and name information, the user enters the desired phone and name information (Step S102) then has a choice to enter another name and phone number (Step S104). If the user desires to enter another phone and name number (Yes in Step S104), the programming procedure returns to Step S102. If the user does not wish to enter any more phone and name numbers (No in Step S104), the user selects the RUN option (Step S105) and the device returns to the OPERATE mode. If the user chooses to enter meal time information in Step S101, the user enters the desired meal times for breakfast, lunch, and dinner in Step S103. After the desired meal time information is entered, the user selects the RUN option in Step S105 to return the device to the OPERATE mode.

Wireless Output

Figure 7:
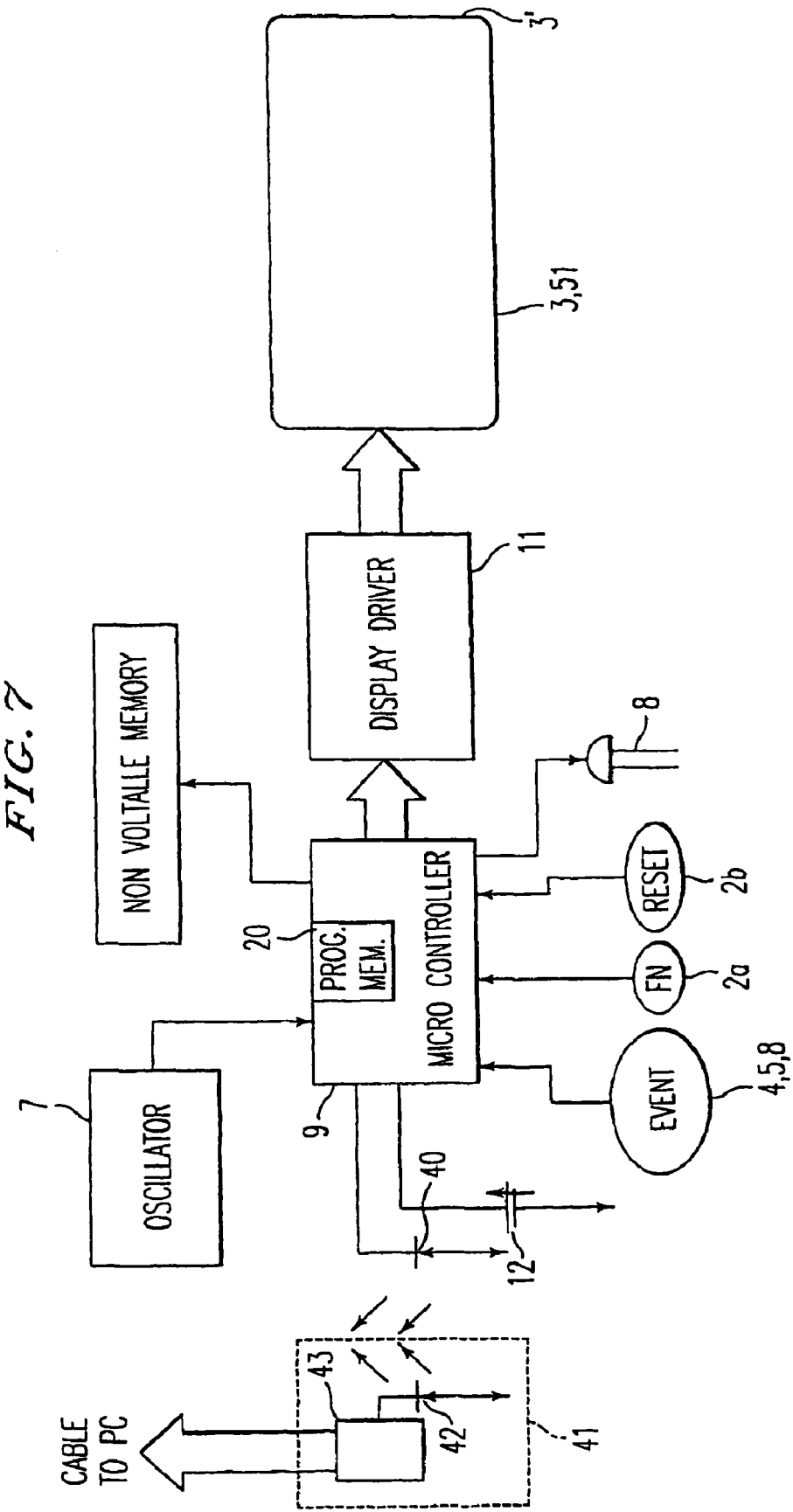
FIG. 7 is a block diagram of a prescription compliance device including a memory for recording the takings of medication and wireless programming capabilities.

FIG. 7 illustrates a third embodiment of the present invention. Since the programming and operation of the prescription compliance device according to this embodiment are identical in most aspects to those of the first and second embodiments, a description of the identical features will be omitted. Referring to FIG. 7, the prescription compliance device further includes a wireless transmitter/receiver 40 (Microchip Part No. SFH485) which communicates with an external wireless transmitter/receiver 41 via a wireless link (not shown). The external wireless transmitter/receiver 41 includes a wireless transmitter/receiver 42 and an interface 43 for connection to an input device, such as a personal computer (PC). The interface is preferably a standard RS-232 serial interface, and infrared technology is employed in the preferred embodiment to transmit and receive information. The personal computer runs software by which the device may be programmed via the personal computer instead of directly programming using the function buttons. The above-described programming procedures for the first and second embodiments are carried out in this embodiment on a personal computer. Programming the device is thus made more convenient by simply inputting the above-described parameters (time, meals, number of pills, etc.) via a personal computer keyboard.

The information input by the patient or his medical care provider via a personal computer is transmitted by the wireless transmitter/receiver 42 and received by the wireless transmitter/receiver 40 and processed just as if it were directly input via the buttons described for the first and second embodiments. The wireless transmitter/receiver 40 transmits back to the external device the current status of the device and the information displayed on the display 3,51.

The device of FIG. 7 also includes a non-volatile memory 10 which records the taking of each dose of medication by the patient when the event switch 4,58 is pressed. Information as to which doses have been taken is accessible via the wireless link so that a physician can examine the patient's compliance in taking the medication. The non-volatile memory 10 of the preferred embodiment is an 8 KB serial EEPROM (Microchip Part No. 24LC08B), however equivalent memories may be employed without departing from the scope of this invention. After programming the device on a personal computer, the patient's operation of the device is identical to that described above for the first and second embodiments.

The wireless transmitter/receiver 40 preferably utilizes Amplitude Shift Keying (ASK) modulation to transmit/receive infrared energy to/from the external wireless transmitter/receiver. Infrared technology has been disclosed merely for illustrative purposes and other wireless technologies and modulation methods are contemplated to be within the scope of the invention.

In addition, each prescription compliance device has a unique identification number assigned thereto and stored in its program memory 20 for the purpose of identifying a particular device when programming from a remote location.

With regard to programming the device, parameters such as the day, time of day, and other parameters may be set in a global register, whereas medication specific parameters are programmed within a unique register. An additional capacity may be included to allow the user to review the information programmed into the device for each of the registers and to review any other pertinent information. This information may be reviewed at the level of the device itself and/or through the wireless computer interface.

The activation of the event switch 4,58 will cause temporal data to be stored in a non-volatile memory. In addition, such temporal data will have associated with it an identifying character so that a utilization of a specific medication or therapy can be tracked.

In addition to or as an alternative to identifying the individual registers by characters or symbols, the device may also provide user-friendly information, such as information identifying the specific medication associated with a register by name or description (i.e. yellow pill, water pill, etc.). Additionally, instructions may be provided in conjunction with an alarm providing the user with useful information (i.e. take with food; avoid milk, etc.). Both types of such additional information would be accessible to each register to recall and display at appropriate times in either voice or character formats as discussed below.

The wireless emissions of the device can also be used as transducing the elements to activate secondary apparatuses. Thus, the emission of a wireless signal in conjunction with an alarm can be used as a signal to activate secondary alarms. The secondary alarms can be used to alert individuals who are hearing or vision impaired, to alert delivery systems to dispense medication to individuals who are mentally or physically handicapped, or to activate any of a variety of other types of apparatuses.

Within institutional settings, emissions from the prescription compliance device which are triggered by the alarm logic, may be used in conjunction with medication or therapy dispensing stations, or similarly, to alert staff that the time has arrived to provide a specific medication or therapy to a patient. Thus, according to the present invention, scheduling and planning of therapy regimens in the pharmacy, by the physician, or by any other care provider, may be programmed into the prescription compliance device. In this embodiment, the device can perform a function of instructing staff to provide medication or therapy in a prescribed manner and/or at prescribed times.

In the present invention, this prescription compliance device is equipped with a capacity for wireless emissions that are output in conjunction with activation of the event switch or passively by opening the medicine bottle, etc. The wireless emissions carry the unique unit specific signature and can be collected by independent receivers. Therefore, collection of emission data can be used to evaluate and monitor the appropriate dispensing of medication and therapy, and to provide an alert/alarm condition if serious omission or error occurs (e.g., a medication was not dispensed properly).

Wireless emission output may also be used to effect concurrent signal emission by another apparatus or device. Concurrent wireless emission by the prescription compliance device and other apparatuses could be received by an independent recorder in very close time sequences, thus allowing temporal and proximity relation of action and instruments to be established. For example, the activation of the "Event Switch" on a prescription compliance device would emit a signal that would be collected by the independent receiver and would also cause an appropriate patient identifying device to emit a signal. This signal would also be collected by the receiver. Through correlation of the receiver identity, prescription compliance device identity, and patient identity, a data set can be generated establishing a relationship between a specific action, a specific place, a specific medication, and a particular patient.

Attachments

Figure 8A:
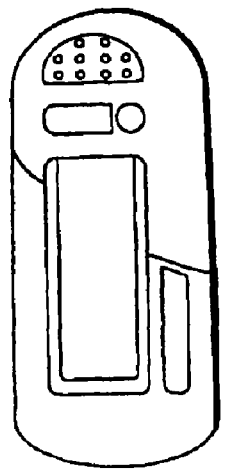
FIG. 8A illustrates the prescription compliance device according to the present invention as a free standing device.
Figure 8C:
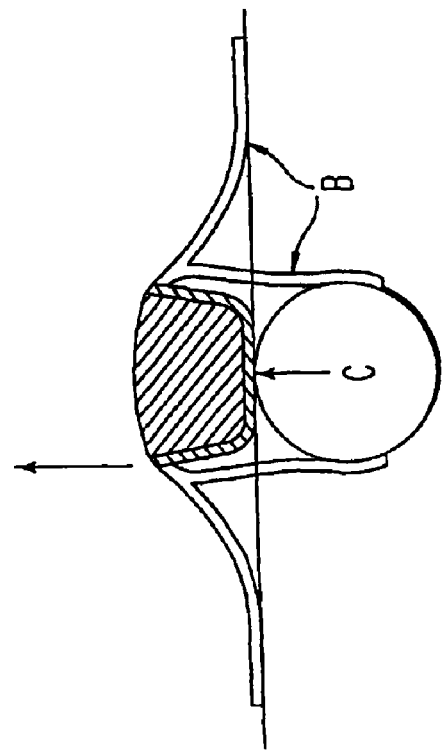
FIG. 8C illustrates a cross-sectional view of the prescription compliance device attached to a bottle according to the present invention.
Figure 8B:
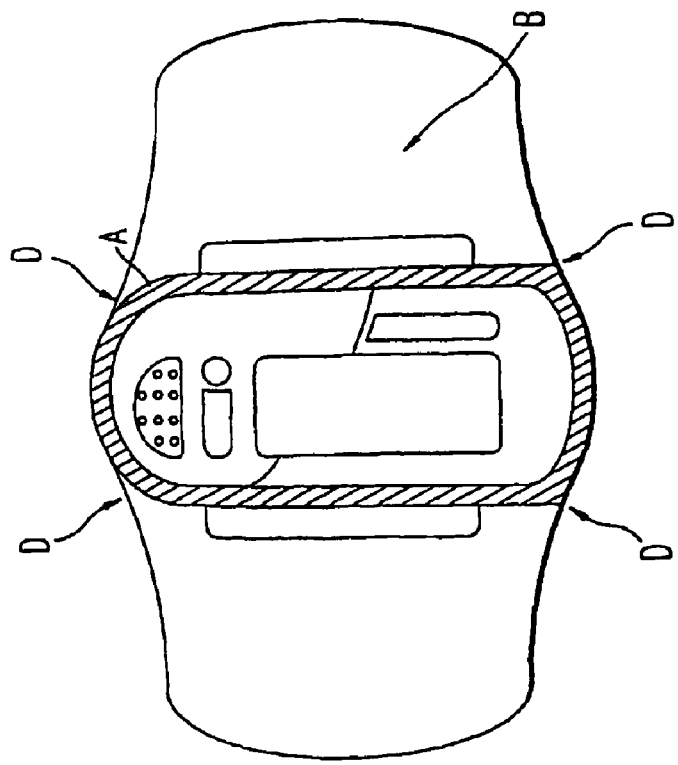
FIG. 8B illustrates a top view of the prescription compliance device and attachment mechanism according to the present invention.

FIGS. 8A, 8B and 8C illustrate the prescription compliance device attached to a variety of containers and surfaces that are either flat or curved. FIG. 5A shows the prescription compliance device as a free standing device which is housed in a plastic casing that has an accommodation on the back surface to permit attachment to a chain or loop that facilitates use as a key chain or pendent (not shown). The device fits into a collar (A in FIGS. 8B and 8C) that are flexible and can bend to accommodate the shape of curved containers or flat surfaces. The "wings" and back surface of the collar are coated with adhesive which attaches the attachment appliance to the surface or container (FIG. 8C). In applications where a narrow construct is required, the "wings" may be clipped off at points D (in FIG. 8B) and attachment to the surface can be achieved solely through the adhesive on the back of the collar C (in FIG. 8C)

Thus, the prescription compliance device according to this invention may be attached to medication containers by adhesives, straps, velcro, mechanical attachment, integration as a component of the container itself, or by any other manner of attachment. The device also operates freestanding, and need not be attached to a medication container.

The device can be utilized in conjunction with or as a part of a wide array of medicine delivery systems and free standing units. Free standing units independent of the medical container include use as, or as a part of a clock, pendent, key chain or watch. Other free standing applications include configurations similar to those used for beepers or cellular telephones or any other similar configuration that can easily be carried by a person. In addition to attaching the device to the medicine container or integration as a part of the medicine container, the current invention describes prescription compliance devices that can be used with or are a part of blister packaging, medicine cabinets, pill box or any other container intended for distributing medication. Additionally, the device can be integrated with, or used in conjunction with a cabinet, cart or other similar apparatus that is used in conjunction with dispensing medicine or therapy in an institutional setting.

Alarms

As discussed above, the device triggers circuits to alert the patient when to take a dose of medication. These alarm capabilities include, in addition to audio and visual signals, tactile signaling, such as a vibrator or comparable mode of signaling, voice signaling achieved through a recording or digital generation, and the use of a wireless output as a transducing element to activate a triggering of secondary devices (e.g., alarms, patient assistance equipment, etc.) or to alert medical personnel or other personnel that some form of action should be taken (e.g., providing medication or therapy). The avenue via which the prescription compliance device communicates information to the user includes tactile and visual and auditory signaling.

The use of tactile stimulation, such as the vibrator used in a pager, or some similar stimulus will provide the user with a discrete signal that can alert the user without alerting others in his/her company. Operation of a tactile stimulation will occur in a manner analogous to that described for the visual and auditory stimuli.

The device according to the present invention also includes the use of recorded signaling to provide the user with identification and/or instructional information. In order for prescription devices to achieve these capabilities, they may be equipped with a microphone, speaker and solid state recording device. In the recording mode, the user can provide vocal input regarding identification of medication and/or proper usage. Utilization of user (or medical care provider) recorded information will occur per logic employed at the level of the device's microprocessor(s) and may incorporate prerecorded information in addition to that recorded by the user. Thus, with the multi-medicine device described, the logic in a specific register may be used to dictate playback of a recorded sequence such as "10 PM; Take Yellow Pills; Take with food." Such a sequence may combine user recorded and prerecorded signaling to alert the user to therapy identification, the time of utilization, special instructions, and any other parameters that might be appropriate. Such sequences are appropriately utilized within specific registers in multi-medication devices, thus providing the user with the proper timing and practical advice for the correct use of specific medications.

In addition, a user initiated action may be required to initiate the display of either visual or recorded identification and instructional information. Thus, the prescription device may first emit an audio, visual or tactile stimulus, and then an action by the user will cause the device to display the appropriate audio and/or visual information. Display of such audio or visual information may be accomplished in a manner so as to preserve the privacy of the user in hearing or viewing such information (e.g., an ear phone).

The device is preferably configured to include six different alarm sounds. For example, when it is time to take the medication, an alarm1 is sounded for approximately 15 seconds, every ten minutes. If the user is unable to take the medication, any button may be pressed to silence the alarm. The TAKE display is also updated to display the latest TAKE at the occurrence of a new take alarm or the clock alarm. An alarm2 occurs when a take event is recorded by selecting the TAKE 61 key. An alarm3 is produced when a skip event is recorded by pushing the SKIP 62 key. When any menu or other selection is made by pushing the SELECT 53 key, an alarm4 is sounded. An alarm5 is produced to notify the user to renew the battery or to refill a prescription. An alarm6 is produced to notify the user that the alarm clock is active. Note the alarm type selection only decides what type of alarm is activated at the time for a "take" event. Other audio alarms (alarm2 to alarm5 are active for both cases, even when the vibration alarm is selected).

The alarm1 is a repeating one short, one long beep; the alarm2 is two short beeps; the alarm3 is one long beep; the alarm4 is one small beep; the alarm5 is two long beeps; and the alarm6 is five short beeps repeated three times. All alarm sounds are preferably disabled for six seconds in the case of a device power failure or when batteries are replaced. Other alarm sounds may also be used.

Dosing Schedules

TABLE 1 summarizes dosing time intervals for morning, midday, afternoon, etc. Normally a patient is awake for 14 hours and it is over this interval that a patient is most likely to take medication prescribed in a given day. The 14 day is divided into a series of time intervals desirable for the patient to take medication. Alternatively, the dosing time intervals may correspond to meal times (e.g., with, before, and after breakfast, lunch, etc.).

TABLE 1

| DOSAGE TIME | INCREMENT | TIME (example) |
| --- | --- | --- |
| $1^{st}$ (Morning) | 0 hr | 8 AM (first dose of day) |
| $2^{nd}$ (Mid day) | 4 hr | 12 PM |
| $3^{rd}$ (Afternoon) | 7 hr | 3 PM |
| $4^{th}$ (Evening) | 9 hr | 5 PM |
| $5^{th}$ (Late evening) | 12 hr | 10 PM |
| $6^{th}$ (Bedtime) | 14 hr | 10 pm |

FIG. 9 illustrates additional programming regimes which allow the user to easily adjust a mediation taken.

Utilization of the specific times generated in such a matrix as shown in Table 1 allows simple definition of appropriate times for the patient to take medication under the most common regimens identified in FIG. 9 as Regimens 1, 2, 3 and 4. Medications not prescribed by these straight forward regimens may be handled by additional regimens. Regimen 0 is a fully custom regimen which allows the patient to define up to, for example, 9 specific times in a day when medication is to be taken. Regimen 5 is designed for medications that must be taken at prescribed intervals and may accommodate intervals of up to 99 hours. Regimen 6 operates to define a specific interval after taking a dose of medication prior to which another dose should not be taken. Regimen 7 defines a monthly cycle for taking medication (i.e., the patient is advised when to and when not to take medication over the course of a month or other cycle). Regimens 8, 9, and 10 are for use with medications that are to be taken in conjunction with meals. These regimen may have default times of 8:00 AM, 12:30 PM, and 6:00 PM, but the patient is able to set times appropriate for his own schedule. Regimen 11 is for use with medications that are to be taken on an empty stomach. Regimen 12 defines a fixed cycle for taking medication, Regimen 13 defines start and stop dates on which a selected regimen is to be begin and end, and Regimen 14 defines selected days on which the medication is to be taken. Regimen 15 is a record only mode where only activation of the event button is recorded.

Programming the regimens shown in FIG. 9 is similar to the programming steps described in the first and second embodiments. Briefly, to program one of the regimens in FIG. 9, the user sets the current time of the day and selects a desired regimen number. To program regimen 0, the times for T1-T9 are set. The chain of times may be terminated by setting 0:00. For Regimens 1-4, the time for the first dose to be taken is set and the take times are automatically calculated as appropriate.

For Regimen 5, the time for the first dose to be taken and the desired time interval is set. The time interval may be set as any number between 0 and 100 or it may be selected from the sequence 1, 2, 3, 4, 6, 8, 12, 24, 36, 48, 60, 72, 84, 96 hr. The take times are automatically calculated by adding the interval time to the first dose time or the previously calculated take time.

For Regimen 6, the time interval is set as any number between 0 and 100 or it may be selected from the sequence 1, 2, 3, 4, 6, 8, 12, 24, 36, 48, 60, 72, 84, 96 hrs. The take times are automatically calculated by adding the interval time to the time the first time or the previously calculated take time. When the user selects this regimen, the option is given to set the minimal interval in hours. The window to take the medication is active once the regimen is set, or appropriately activated. When the medication has been taken, the device counts the time integral before the take window reopens. Visual alarms for the take events associated with the asNEEDED (Regimen 6) regimen may be displayed as OK TAKE.

For Regimen 7, the time for the first dose to be taken is set. Then the days on (i.e., the number of consecutive days in which the prescription should be taken) is set. The days in the cycle (i.e., days in month or number of days), and the current date or number of days in the cycle is set. The starting date in the cycle is set and the take times are automatically calculated. The device additionally advises the user on what days in the cycle medication should be taken. When the user enters the first take time in a new cycle, the device will prompt the user to enter a new value for the day in the cycle. For example, assume the user wanted to take medication from the 16th to the 25th of each month and today is April 9th. In this case, Day ON=10, Days in Cycle=30, Current Date=9, and Starting Date=16. These take dates will repeat month after month with the provision that take events don't occur after the 28$^{th}$ day of any month. If the device is equipped with an electronic perpetual calendar the same result can be achieved by simply entering the monthly start and stop dates.

For Regimen 8, the user set or default time for Breakfast (8:00 AM), Lunch (12:00 PM), or Dinner (5:00 PM) are the times at which the patient is instructed to take medication. The ranges are set at 15 min before the mealtime up until 60 min past, for example.

For Regimen 9, the user scans and selects a default time for Breakfast (08:00 AM), Lunch (12:30 PM), and Dinner (6:00 PM) (and may alter the default time) and the take times are automatically calculated by adding 2 hours to the selected meal times.

For Regimen 10, the user scans default times for Breakfast (08:00 AM), Lunch (12:30 PM), and Dinner (6:00 PM) (and may alter the default time) and the take times are automatically calculated by subtracting 1 hour from the selected meal times.

For Regimen 11, the take times are the meal times plus two hours with an acceptable range of −15 minutes to +60 minutes. With both the EMPTY STOMACH and WITH FOOD regimens, alternative take times and take regimens may be equally acceptable. Once either the EMPTY STOMACH or the WITH FOOD regimen is selected, the user may select between turning ON or OFF this regimen for any given meal. The user can thus choose between taking medication once a day in association with any meal, twice a day in association with any two meals, or three times a day in association with all three meals. The setting of the meal times in the device is structured so that the minimal interval between breakfast and lunch is 4 hours, the minimal interval between lunch and dinner is 5 hours, with the additional feature that all meal times occur within a 14-hour period.

For Regimen 12, the user has an option to create a repeating protocol of take days and off days. This is achieved by providing the user with the option to select the total number of days in the cycle, starting on the first day of the cycle on which medication is to be taken, and which day of the fixed cycle is today's date. Once this data has been entered, the user is given the option to select the time of day at which time the medication is to be taken. The take range is plus or minus 4 hours.

For Regimen 13, the user is given the option to specify a start day and time and an end day and time for any of the other regimens. When this regimen is selected, the user is given the option to enter a month, date and time when the regimen is to start, and also is given the option to set the month, day and time when the regimen is to end. Once these parameters have been selected, the user is given the option to select between the several regimens that are available. Subsequent programming of the regimen is achieved by the sequence of data entry that is normal to that regimen.

For Regimen 14, the user is given the option to select on which days of the week to take a medication. Once this regimen is selected, the user is given the option to scan through the days of the week (i.e., Sunday to Saturday) and for each individual day to select an ON or OFF option. Once these parameters are entered, the user is given the option to select the time of day at which the medication is to be taken. The take range is plus or minus 4 hours.

Figure 10:
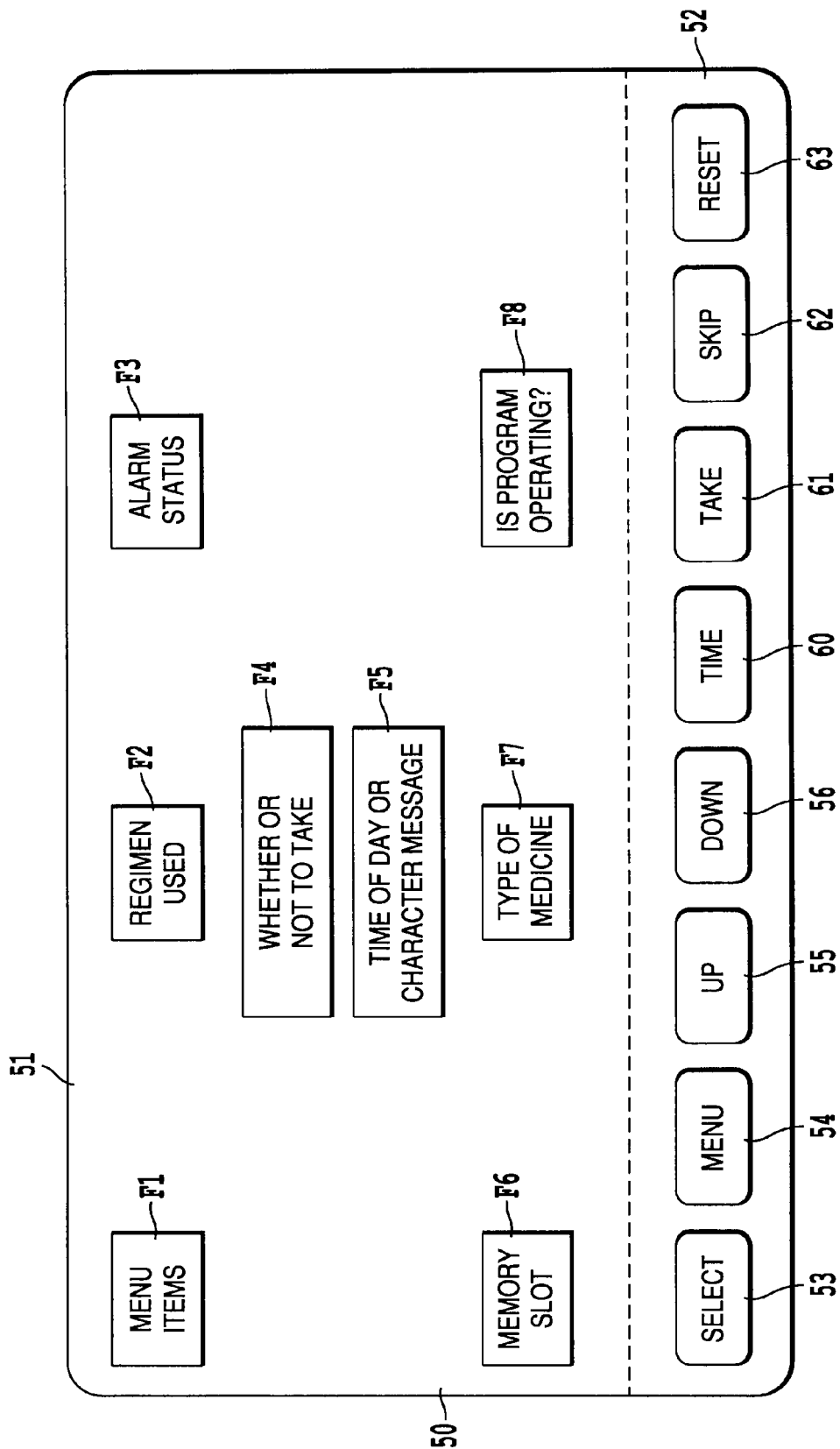
FIG. 10 is an illustration of a prescription compliance device in accordance with a fourth embodiment of the present invention.

Turning now to FIG. 10, which illustrates a block diagram of the prescription compliance device 50 according to a fourth embodiment of the present invention. As shown, the display fields F1-F8 shown in FIG. 5 are also used in the device 50 according to the fourth embodiment. However, the key pad 52' includes additional keys: TIME 60, TAKE 61, SKIP 62 and RESET 63. These keys are used in programming and operating the device in the fourth embodiment, which will now be described with reference to FIG. 11.

Figure 11:
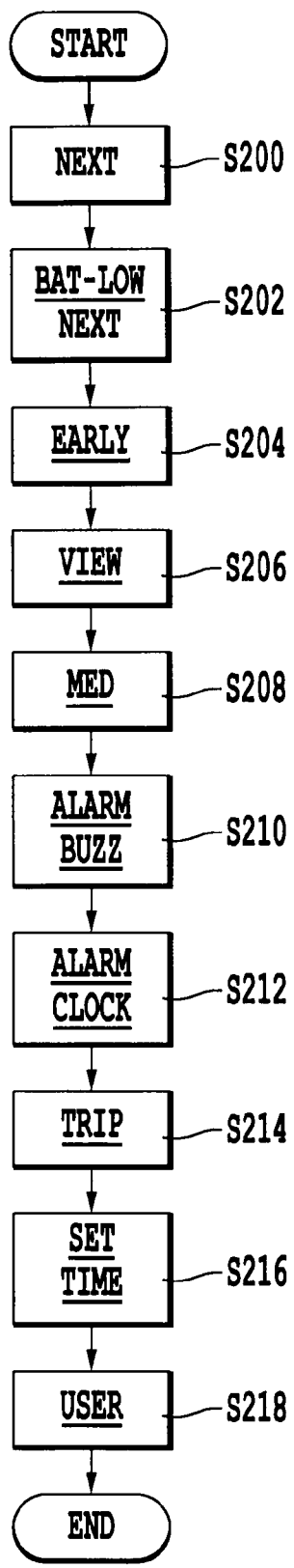
FIG. 11 is a flow diagram illustrating menu choices available to the user.

In more detail, FIG. 11 illustrates the choices available to the user which can be scrolled through by pressing the MENU 54 key. The menu choices are displayed in the display field F1 (see FIG. 10), and include the options of NEXT (step S200), BAT-Low (step S202), EARLY (step S204), VIEW (step S206), MED (step S208), ALARM BUZZ (step S210), ALARM CLOCK (step S212), TRIP (step S214), SET TIME (step S216) and USER (step S218). The user may scroll through the options by pressing the MENU 54 key and then select the desired option with the SELECT 53 key. The following is a description how a user operates each of the menu options steps S200-S218.

Figure 12A:
FIG. 12A-12B illustrates an operation of the NEXT and TAKE menu options.
Figure 12B:
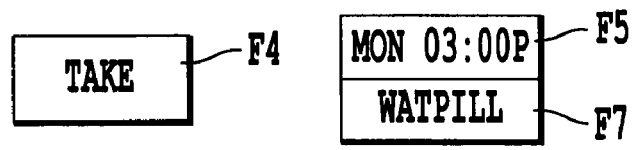

In more detail, FIG. 12A-12B illustrates fields F5 and F7 displaying information when the NEXT menu option is selected. As shown, a water pill is next to be taken on Monday at 3:00 P.M. Note, if the battery is low, the NEXT menu option will appear as that shown in step S202 (i.e., the display field F1 indicates the battery is low). The battery indication occurs after the passage of certain number of days from when the battery was last replaced, or a low battery condition may be physically measured, for example. Thus, the user is given the option to either replace or recharge the batteries. If an alarm to take a medication becomes active the information in F7 and F8 shown in FIG. 12B will be shown. When the device alerts to take a medication the TAKE in F& will flash to bring attention to the visual alarm. The time that the alarm activated will be displayed.

Figure 13A:
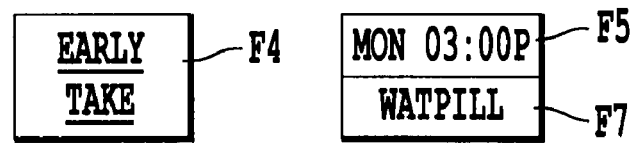
FIGS. 13A-13E illustrate an operation of the EARLY menu option.
Figure 13B:
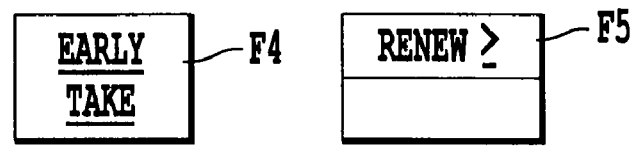

FIGS. 13A-13E illustrate an operation of the EARLY menu option step S204. As shown in FIG. 13A, when the EARLY menu option is selected, the display fields F4, F5 and F7 indicate that one or more medications are within the early take range allowed or that possibly one or more medications need to be renewed. Pressing the UP and DOWN keys 55, 56 allow the user to scroll through the list of medications that may be taken early or that need to be renewed. FIG. 13B indicates that there are no medications currently in the early take range, but that there is at least one medication that needs to be renewed. If the prompt "MULTI" also appears in display field F4 (see FIG. 13D), this indicates that more than one medication is to be renewed. The MULTI prompt disappears on the last medication requiring renewal (see FIG. 13E).

Figure 13C:
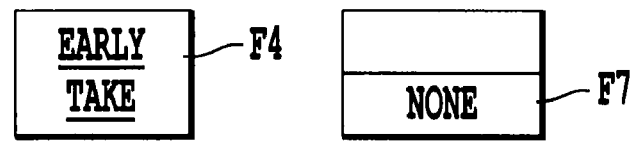
Figure 13D:
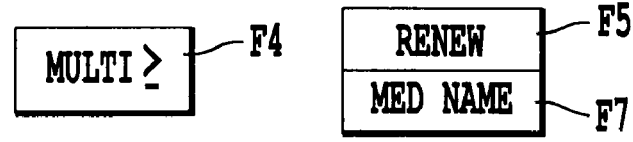

FIG. 13C illustrates that there are neither any medications in the early take range nor are there any medications that require renewal. If the MENU 54 key is pressed when the user is inside the EARLY take mode, the device returns to the EARLY menu option shown in step S204. Note, the TIME 60 key, if selected, will display the current time in display field F5 for 30 seconds until it is released and then the device returns to the last displayed field. If no other key is pressed within 20 seconds, for example, the display field F1 will return to the TAKE menu option or another appropriate default option. When the NEXT screen is active pressing TIME will cause a continuous display of the current time until TIME or MENU is pressed, or until an alarm becomes active.

Figure 13E:
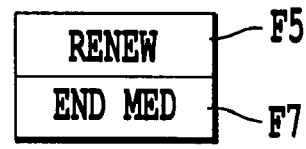

As noted above, FIG. 13D indicates there are more medications to be renewed. In addition, the multi display appears when there are multiple medications that can be taken early. The user enters take or skip events into the device by pressing either the TAKE or SKIP keys as desired. To minimize errors the user is required to press the key twice for confirmation. Once this has been done the device will advance to the next medication for which an early take is active, or to a renew alert. FIG. 13E indicates this is the last medication in the renewal list (note the MULTI prompt is not displayed).

Figure 14:
FIG. 14 illustrates an operation of the VIEW menu option.

Turning now to FIG. 14, which illustrates the operation of the VIEW menu option step S206. In more detail, selection of the VIEW menu option causes the information in fields F4, F5 and F7 is displayed as shown in FIG. 14. Using the UP and DOWN keys 55, 56, the user can view the schedule for taking medications arranged in ascending chronological order including appropriate time and medicine information. For example, up to a maximum of 99 future take events occurring over the next 7 days can be thus viewed. Returning to the NEXT display option step S200 or other appropriate screen is accomplished by a 20-second time out (i.e., an UP or DOWN key 55, 56 is not pressed within 15 seconds). Other time out values may also be used. Pressing the MENU 54 key returns the device to the VIEW display option step S206.

Figure 15A:
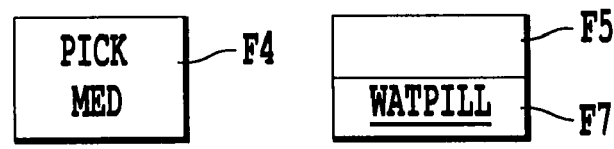
FIGS. 15A-18B illustrate an operation of the MED menu option.

Turning now to the MED menu option step S208 with reference to FIGS. 15A-18B. In more detail, FIG. 15A illustrates information display when the MED menu option is first selected. As shown, the field F4 displays PICK MED and field F7 displays an acronym for a water pill. The UP and DOWN keys 55, 56 may be used to scan among the different medications. If one of the medications shown in field F7 is selected via the SELECT 53 key, the information shown in FIG. 15B is displayed. The user may then view different information about the selected medication (which is discussed in greater detail later).

Figure 15B:
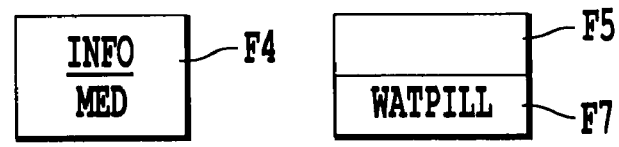
Figure 15C:
Figure 15D:
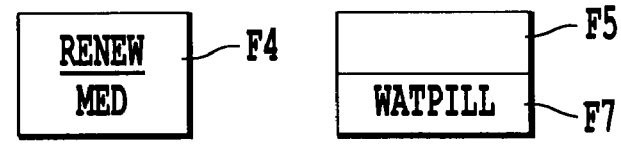
Figure 15E:
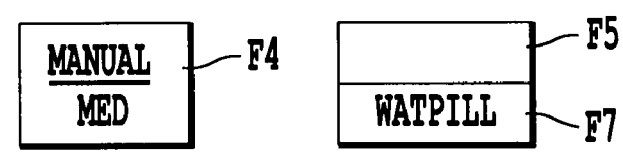
Figure 15F:
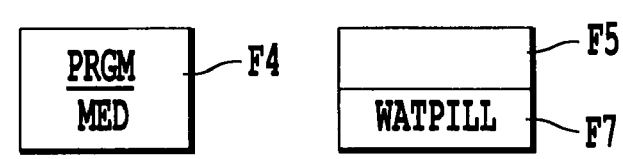

FIGS. 15C-15F illustrate different options which may be scrolled to in addition to FIG. 15B. In particular; the sub-options of the selected PICK MED option shown in FIG. 15A includes information about the medication (FIG. 15B), the status of the medication (FIG. 15C), whether or not the medication is to be renewed (FIG. 15D), information about manual options (FIG. 15E), or entry into a mode that allows programming of the medication and the appropriate regimen (FIG. 15F). Note the status, renew and manual sub-options may not be displayed if the device is locked, and the program option is preferably disabled if the device is locked.

Figure 16A:
Figure 16B:
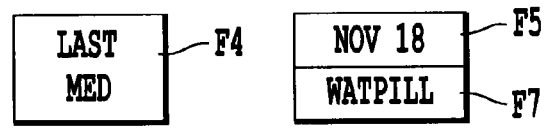
Figure 16C:
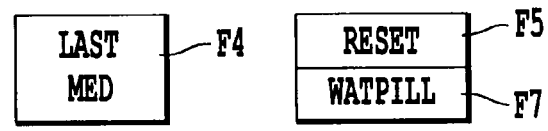
Figure 16D:
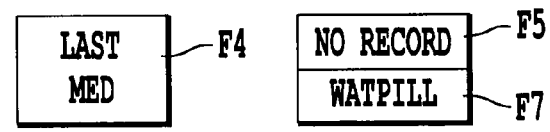
Figure 16E:
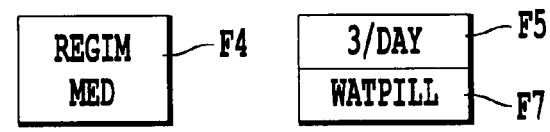
Figure 16F:
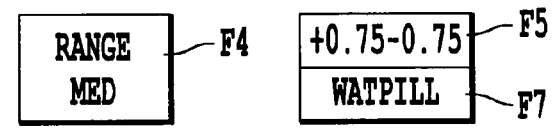
Figure 16G:
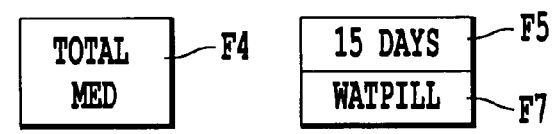
Figure 16H:
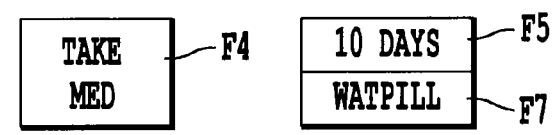
Figure 16I:
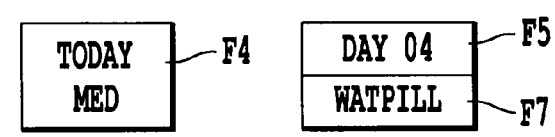
Figure 16J:
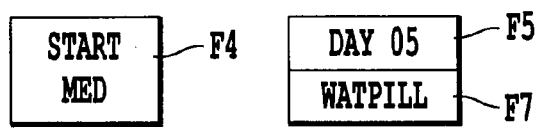
Figure 16K:
Figure 16L:
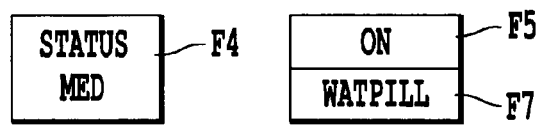
Figure 16M:
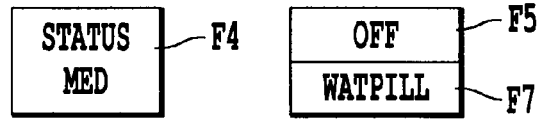
Figure 16N:
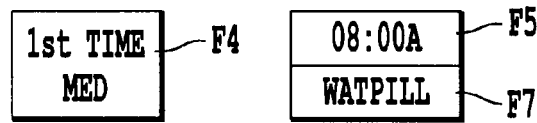
Figure 16O:
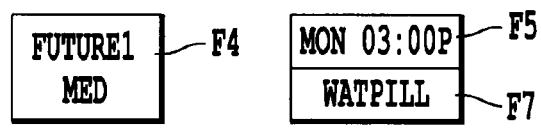
Figure 16P:
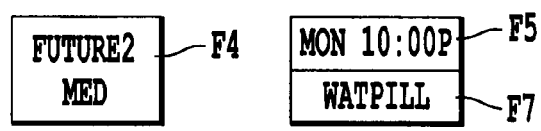
Figure 16Q:
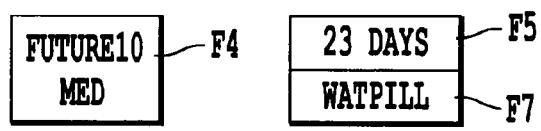
Figure 16R:
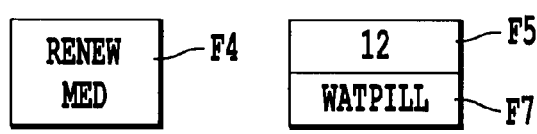

FIGS. 16A-16R illustrates different options performed for the INFO MED sub-option shown in FIG. 15B. In more detail, selection of the sub-option INFO MED shown in FIG. 15B results the display shown in FIG. 16A. As shown, the last time the water pill was taken was on Monday at 8:27 A.M. as defined by the fields F4, F5 and F7. If the last event occurred more than 7 calendar days ago, the information shown in FIG. 16B is displayed. As shown, the field F5 indicates that the last water pill was taken on November 18. Alternately, the display may show the number of days that have elapsed since the last dose of water pill was taken.

In addition, to block entry of erroneous information into the last MED sub-option shown in FIGS. 16A and 16B, the information shown in FIGS. 16C and 16D are displayed at start-up, reset or modification of the given MED program. Further, using the UP or DOWN keys 55, 56 results in the type of regimen being displayed as shown in FIG. 16E. As shown, the regimen type is displayed for the particular medication in field F5, which displays the three times a day regimen #3 shown in FIG. 9). Depending on the regimen, successive entries of the UP or DOWN keys 55, 56 results in the information shown in FIG. 16F. As shown, the information includes the range values for the particular selected regimen as shown in the fields F4, F5 and F7. FIGS. 16G-16I illustrate the total number of days for the fixed cycle regimen, the number of days the medication is to be taken in the fixed cycle regimen, and which day of the fixed cycle is today's date, respectively.

FIGS. 16J and 16K illustrate information displayed for the MONTH CYCLE regimen #7 shown in FIG. 9. In more detail, FIG. 16J indicates the starting day of the MONTH CYCLE that the medication is to be taken, and FIG. 16K indicates the last day of the MONTH CYCLE that the medication is to be taken, inclusive of the day specified. Following the above regimen displays, either of the status displays shown in FIGS. 16L and 16M is provided to the user. In particular, FIG. 16L displays the information indicating the medication is ON and should be taken at the medication alarm times. Using the UP key 55 in this display proceeds to a display indicating the first time of day the medication is to be taken (as shown in FIG. 16N). Further, if a medication is to be renewed, the appropriate renew information is displayed (as shown in FIG. 16R). FIG. 16M indicates the medication alarm is disabled (i.e., OFF). FIGS. 16O-16Q illustrates successive entries of the UP key 55 which displays the next 10 take times for the medications. Note FIG. 16Q indicates that a take occurs later than within the next 7 days. The 23 days shown in field F5 indicates the number of days from today when the medication is to be taken. Thus, with reference to FIG. 16Q, the user can see that the medication must be taken in 23 days. FIG. 16R shows information indicating how many days from today the medication will need to be renewed. The renew alarm is activated on midnight of day 00 of the renew, for example. Thus, with reference to FIG. 16R, the user can determine that the medication must be renewed in 12 days. This information is only displayed if the renew option is on.

Figure 17:
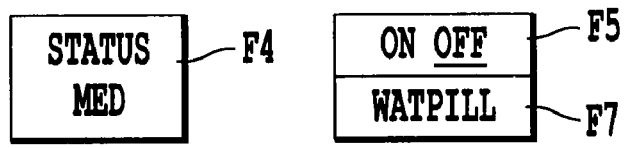

FIG. 17 illustrates information displayed when the STATUS MED sub-option shown in FIG. 15C is selected. As shown, the display field F5 in FIG. 17 indicates the status is OFF. The status may be changed by using the UP and DOWN keys 55, 56 to toggle between the ON and OFF states. The SELECT 53 key is pressed to select ON of OFF and the selection is accomplished by a beep. If the medication has been transitioned from an OFF state to an ON state, the next take alarms are recalculated against the current time.

Figure 18A:
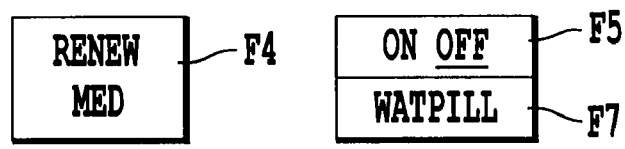
Figure 18B:
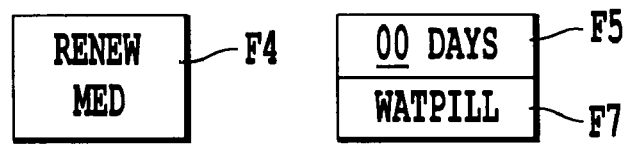

Turning now to the RENEW MED sub-option shown in FIG. 15D. Selection of the RENEW MED sub-option results in the information shown in FIG. 18A. As shown, the RENEW MED sub-option is in an OFF state. The UP and DOWN keys 55, 56 can be used to toggle between the ON and OFF states. Selecting the OFF state via the SELECT 53 key causes the alarm4 to sound and the display returns to the NEXT option step S200 shown in FIG. 11 or other appropriate display. If the renew option is ON and selected, the alarm4 sounds and the information shown in FIG. 18B is displayed. The 00 in field F5 designates the currently registered number of days prior to notification to renew. The UP and DOWN keys 55, 56 may be used to adjust this number between 0 and 99. Pressing the SELECT 53 key causes selection of the designated number. Thus, using FIGS. 18A and 18B, the user can set the particular days in which the medication is to be renewed and may turn ON or OFF this feature. The MANUAL MED and PRGM MED sub-options shown in FIGS. 15E and 15F are described later.

Figure 19A:
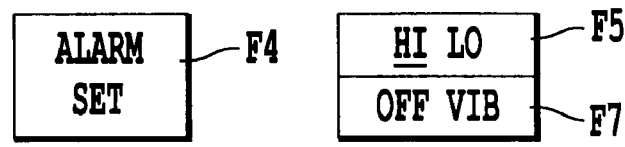
FIGS. 19A-19D illustrate an operation of the ALARM BUZZ menu option.
Figure 19B:
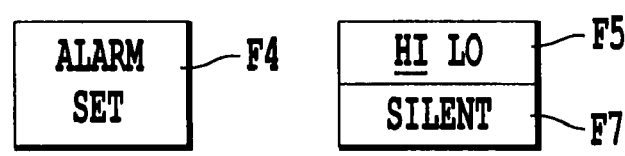
Figure 19C:
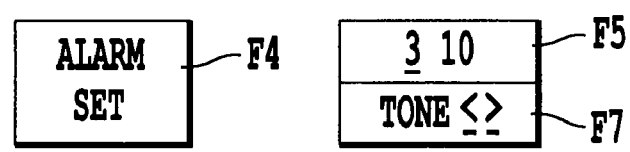
Figure 19D:
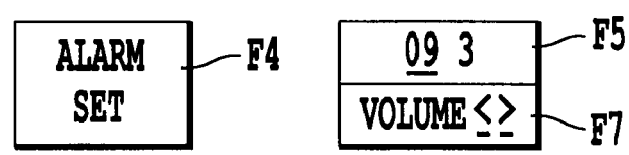

Turning now to FIGS. 19A-19D, which illustrate different options of the ALARM BUZZ menu option step S210 shown in FIG. 11. Selection of the ALARM MENU buzz option results in one of the displays shown in FIGS. 19A and 19B. As shown, the user can toggle between setting the alarm to a high or low sound or vibration and to select the alarm to be ON or silent. As shown in FIG. 19C, the user may set a desired tone for the alarm sound using the UP and DOWN keys 55, 56. FIG. 19D illustrates an option in which the user may adjust the volume for the alarm sound.

Figure 20A:
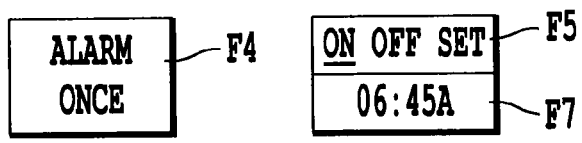
FIGS. 20A-20D illustrate an operation of the ALARM CLOCK menu option.
Figure 20B:
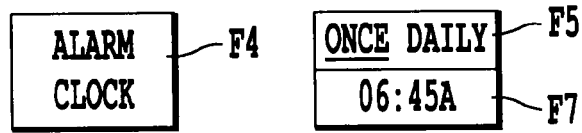
Figure 20C:
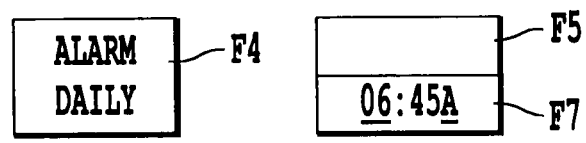
Figure 20D:
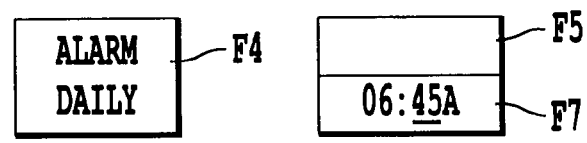

Next, FIGS. 20A-20D illustrate different operations of the ALARM CLOCK menu option step S212 shown in FIG. 11. Selection of the ALARM CLOCK option causes the alarm4 to sound and results in the display shown in FIG. 20A. The time displayed in field F7 is the last time the alarm was set for, and the information about whether the alarm is set to display once or daily in field F4 (note FIG. 20A illustrates the alarm being set to display once). The UP and DOWN keys 55, 56 may be used to scan between ON, OFF and SET options in field F5 and the SELECT 53 key may be used to select one of the options in the field F5. Selection of the OFF option turns the alarm OFF, and selection of the option SET results in the displayed information shown in FIG. 20B. As shown, the user is given the option of scanning between the ONCE or DAILY option in the field F5. Selecting either of the options in the field F5 results in the display information shown in FIG. 20C (as shown in the field F4, the user has selected the DAILY option). The user is also able to set the time at which the alarm is to sound using the UP and DOWN keys 55, 56. Note in FIG. 20D, the user has set an alarm to go off at 6:45 AM each day. Note this alarm is different than an alarm that sounds when a medication has been taken improperly.

Figure 21A:
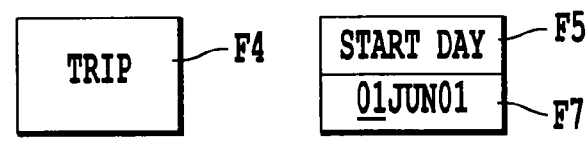
FIGS. 21A-21D illustrate an operation of the TRIP menu option.
Figure 21B:
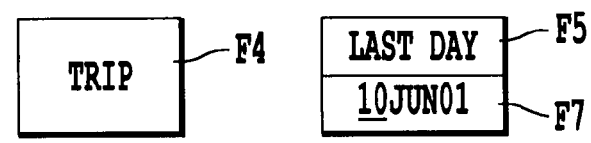
Figure 21C:
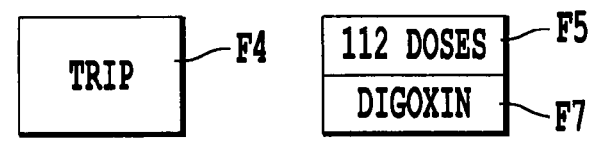
Figure 21D:
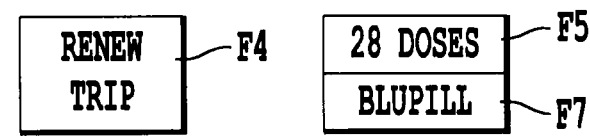

FIGS. 21A-21D illustrate different options for the TRIP menu option step S214 shown in FIG. 11. The TRIP option calculates the amount of medication (in dosage) needed over a specified period between two dates. Selection of the TRIP menu option causes the alarm4 to sound and results in the display shown in FIG. 21A. The user may use the UP and DOWN keys 55, 56 to select the start day. Similarly, as shown in FIG. 21B, the user may select the last day. After the last day is selected, the information shown in FIG. 21C is displayed. The user may then use the UP and DOWN keys 55, 56 to scan among the number of doses calculated for each of the ON medications. For example, as shown in FIG. 21C, the user can see that 112 doses will need to be taken during the start and last days entered into the device. This is particularly advantageous when a vacation or trip is planned. Further, as shown in FIG. 21D, the user can see that the medication should be renewed prior to beginning on the trip. The number of doses are preferably calculated beginning at midnight of the start date through one second before midnight of the day following the last day.

Figure 22A:
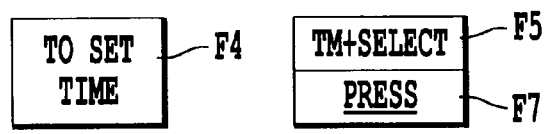
FIGS. 22A-22M illustrate an operation of the SET TIME menu option.
Figure 22B:
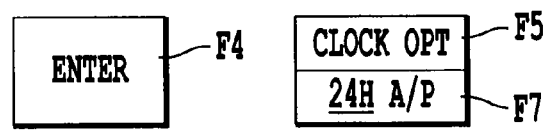
Figure 22C:
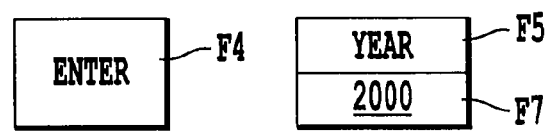

Turning now to FIGS. 22A-22M, which illustrate different options of the SET TIME menu option step S216 shown in FIG. 11. Note this feature is disallowed if the device is in a LOCK mode. With the SET TIME option, the user may change the date and time. Selection of the SET TIME option results in the display shown in FIG. 22A. The information displayed in FIG. 22A indicates the user is to press the TIME 60 key and the SELECT 53 key simultaneously to set the time. When these keys are pressed, the information shown in FIG. 22B is displayed. Here, the user may scroll between the twenty-four hour and AM/PM selection shown in field F7 using the UP and DOWN keys 55, 56. The 24 H option causes all times to be displayed as military time (i.e., 1:15 PM is displayed as 13:15). Selection of the CLOCK option shown in field F5 results in the information shown in FIG. 22C being displayed. Here the user may select the year.

Figure 22D:
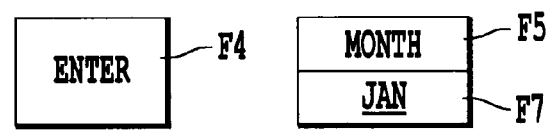
Figure 22E:
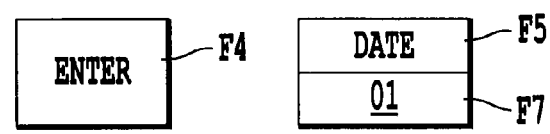
Figure 22F:
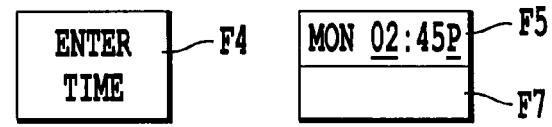
Figure 22G:
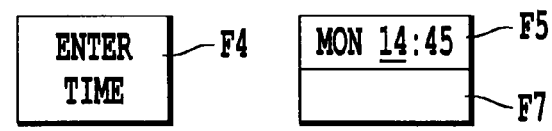
Figure 22H:
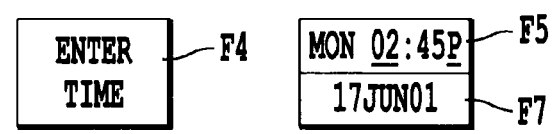
Figure 22I:
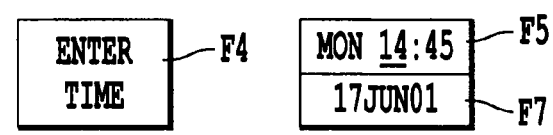
Figure 22J:
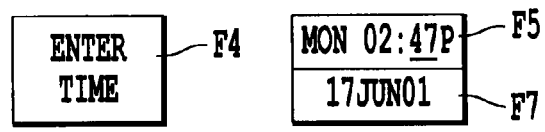
Figure 22K:
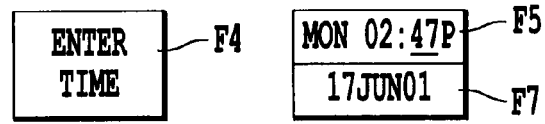
Figure 22L:
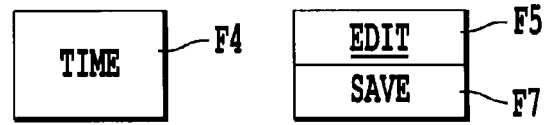
Figure 22M:
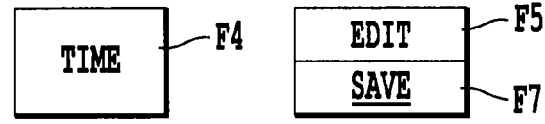

Upon selection of the year, the user may choose the appropriate month and date as shown in FIGS. 22D and 22E. Then, as shown in FIGS. 22F and 22G, the user may select the time of day (note FIG. 22F illustrates the time being displayed in standard AM/PM time, and FIG. 22G illustrates the time being displayed in military time). Further, FIGS. 22H and 22I illustrate a case in which it is not the first time change from when the device was powered up (note the above FIGS. 22A-22E illustrate setting the time when the device is first powered on). FIG. 22H illustrates the case for standard AM/PM time and FIG. 22I illustrates the case for military time. Note in this mode, the hour field can preferably be not changed by more than 4 hours in either direction and the UP and DOWN keys 55, 56 are ignored at the 4 hour limit. Also, the date and day are preferably automatically changed when going backwards from 12:xx AM or forward from 11:xx PM. FIGS. 22J and 22K illustrate the minutes being changed. Thus, in reference to FIGS. 22H-22K, the user may change the hours and minutes of the time. These values are then selected and the alarm4 sounds resulting in the information displayed in FIG. 22L. Here, the user can toggle between FIGS. 22L and 22M to edit the time or save the time.

Figure 23A:
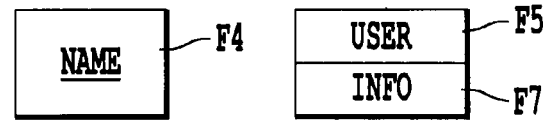
FIGS. 23A-25L illustrate an operation of the USER menu option.
Figure 23B:
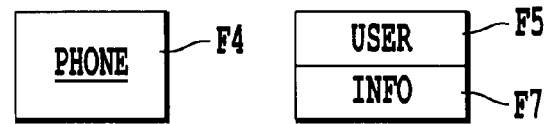
Figure 23C:
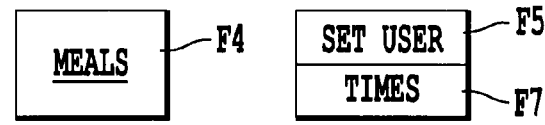
Figure 23D:
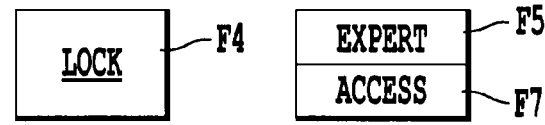
Figure 23E:
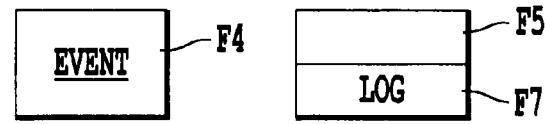
Figure 23F:
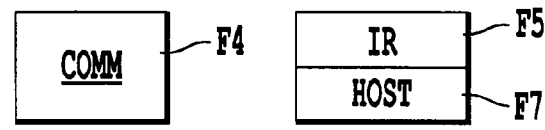

Turning now to FIGS. 23A-23F, which illustrate the different user options the user may scroll through using the UP and DOWN keys 55, 56 in the USER menu option step S218 shown in FIG. 11. In more detail, using the UP and DOWN keys 55, 56, the user may program options including a NAME (FIG. 23A), PHONE (FIG. 23B), MEALS (FIG. 23C), LOCK (FIG. 23D), EVENT (FIG. 23E) and COMM (FIG. 23E). Note some of the USER functions are preferably limited to expert use and cannot be performed when the device is LOCKED. As a programming illustration, selection of the NAME sub-menu option shown in FIG. 23A results in the display shown in FIG. 23G. Here, the user may enter his or her name by using the UP and DOWN keys 55, 56 in conjunction with the SELECT 53 key.

Figure 24A:
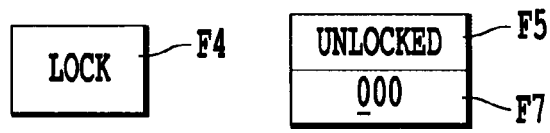
Figure 24B:
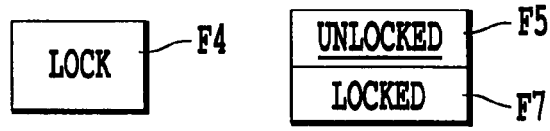
Figure 24C:
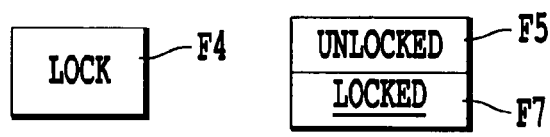

FIG. 24A illustrates selection of the LOCK sub-menu option shown in FIG. 23D. The LOCK option controls limited access to the advance features that may be LOCKED or UNLOCKED by toggling the field F5 using the UP or DOWN keys 55, 56. Further, a three digit code (password) is required to LOCK or UNLOCK the device. Once the code has been entered, selection between UNLOCKED in FIG. 24B or LOCKED in FIG. 24C can be made.

Figure 23G:
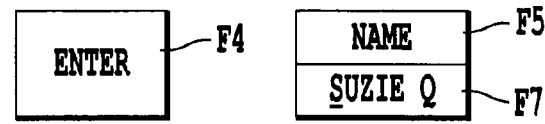
Figure 25A:
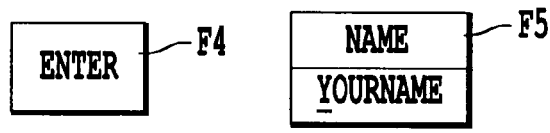
Figure 25B:

FIG. 25A is similar to FIG. 23G and corresponds to the NAME sub-menu option shown in FIG. 23A. Once this information has been entered in FIG. 25A, the user may continue editing this information or save this information using the UP and DOWN keys 55, 56 as shown in FIG. 25B.

Figure 25C:
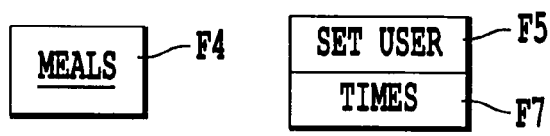
Figure 25D:
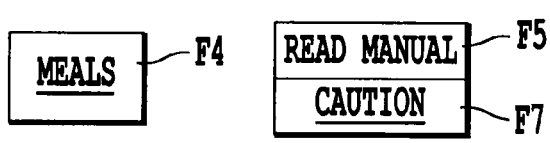
Figure 25E:
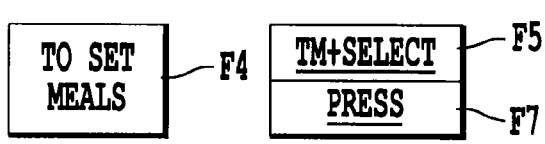
Figure 25F:
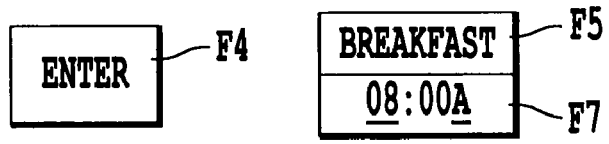
Figure 25G:
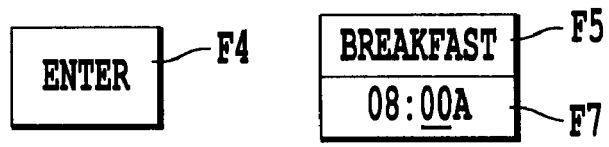
Figure 25H:
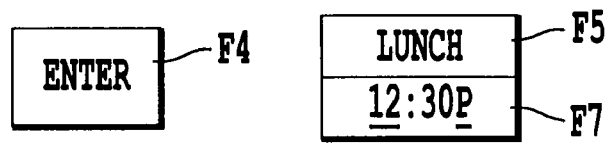
Figure 25I:
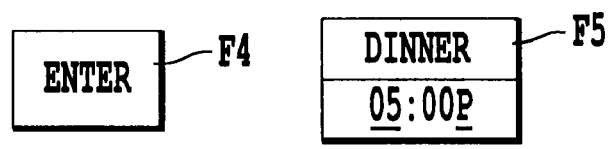

Turning now to the MEALS sub-menu option shown in FIG. 23C. FIG. 25C illustrates the selection of the MEAL sub-menu option in FIG. 23C in which no meals regimens are active (i.e., the user is requested to set the times). Dressing the SELECT 53 key produces the display shown in FIG. 25F. If any medication has a meal time regimen association, the information shown in FIG. 25D is displayed. Note the user is cautioned to read the manual before programming the device. Pressing the SELECT 53 key produces the display shown in FIG. 25E. This display functions in a manner similar to the TIME CHANGE display in that the TIME and SELECT keys 53, 60 are required to be pressed concurrently to proceed with editing the meal times shown in FIGS. 25F and 25I. As shown in FIGS. 25F-25I, the user is able to modify the times the meals are to be taken. That is, the user can set breakfast time to be 8 AM. On the contrary, if the user worked a midnight shift, they could change the breakfast time to be 11 PM, for example.

Figure 25J:

FIG. 25J illustrates an option in which the user is able to continue editing the entered meal time information or to save the information. If the device is in a locked state, the meal times will be displayed by pressing the SELECT 53 key while the display reads as shown in FIG. 25C, but cannot be edited. Breakfast can preferably occur any time with lunch at least 4 hours later and dinner at least 5 hours after lunch. All meals preferably occur within a fourteen hour period, and after the selection of breakfast times, the device is preferably prevented from illegal selection of lunch or dinner times.

Figure 25K:
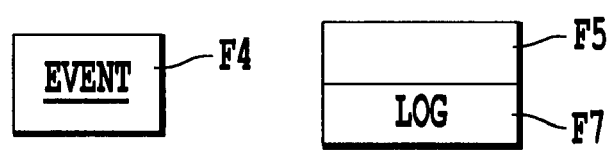
Figure 25L:

Turning now to FIGS. 25K and 25L, which illustrate the operations of the EVENT user sub-menu option shown in FIG. 23E. Selection of the EVENT user sub-menu option results in the display shown in FIG. 25K indicating the user may view a log of the medication thus taken. The UP and DOWN keys 55, 56 may be used to scroll through the log events. An event number greater than 2399 preferably indicates that logging has exceeded 2400 events and has wrapped around, losing the earliest log events. Events logged include TAKE, SKIP, MISS (for missed medications exceeding the TAKE time limit), MCHG (manual medications edit), NTIM (display times at SAVE) and TCHG (displays time at start of EDIT time), for example. Medication log times are saved chronologically at the time the event occurred. As shown in FIG. 25L, the user can see that the last entry in the EVENT log is Viagra on Friday, 8:34 AM. The EVENT log may be cleared by the computer using the IR interface and is preferably not affected by the RESET function. That concludes the description of the user sub-options shown in FIGS. 23A-23F.

Turning now to the operations for programming a regimen (i.e., the PRGM MED sub-menu option shown in FIG. 15F). Programming of regimens for individual medicines is accomplished by first selecting the MED menu option step S208 shown in FIG. 11 and then selecting a medication as shown in FIG. 15A and then selecting the PRGM MED sub-menu option shown in FIG. 15F. Selection of the PRGM MED sub-menu option results in the display shown in FIG. 26A. At this point, the user can enter an acronym for the name of the medication. After the medication name is selected, the user can scan among the regimen options shown in FIG. 9. FIG. 26B illustrates selection of the once-a-day regimen #1 shown in FIG. 9. After selection of the regimen #1, the user enters the time of day in which to take the medication as shown in FIGS. 27A-27B. Upon completion of entering the time of day the medication is to be taken, the user is able to either further edit the entered information or save the entered information as shown in FIGS. 27C-27D.

Figure 29A:
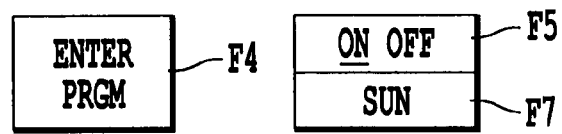
Figure 29B:
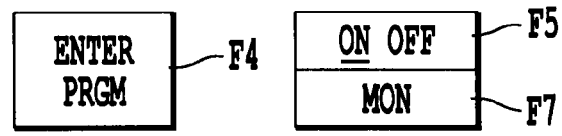

FIG. 28 illustrates the information entered for the AS-NEEDED regimen #6 in FIG. 9. As shown in FIG. 28, the user is able to enter a time interval for this regimen. After the time interval is entered, the user is able to select the time of day similar to that as shown in FIGS. 27A-27B. FIGS. 29A-29B illustrate the operations for programming the DAY of WEEK regimen #14 shown in FIG. 9. As shown in FIG. 29A, the user is given the option to select the appropriate ON/OFF designation for the specified day and can scroll through the days as shown in FIG. 29B. The selection process is repeated until the appropriate designations for each day of the week has been entered. After the information for the last day has been entered, the user is able to enter the time of day at which the medication is to be taken similar to that shown in FIGS. 27A-27B.

The regimens with food, after meals and before meals (i.e., regimen #'s 8, 9, 10 and 11 in FIG. 9) are programmed by selecting the particular regimen. Note, the choice can be made as to which meals are selected. The user can choose any or all of the breakfast, lunch and dinner meals (similar to how is performed in FIGS. 29A and 29B). Once a regimen is selected, a display similar to that shown in FIG. 27C is provided allowing the user to complete the data entry process. Note, it is also possible to only use the empty stomach and with food regimens #11 and #8.

Figure 30A:
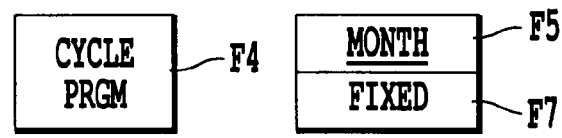
Figure 30B:
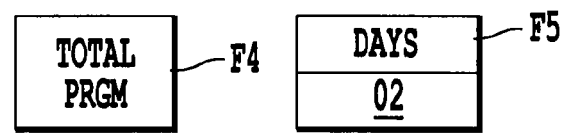
Figure 30C:
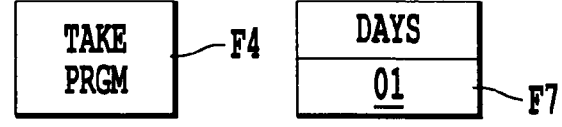
Figure 30D:
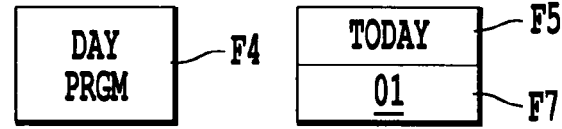

Turning now to FIGS. 30A-30F, which illustrate the operations for programming the FIXED CYCLE regimen #12 and the MONTH cycle regimen #7 shown in FIG. 9. The selection of the CYCLE results in the display shown in FIG. 30A. The UP and DOWN keys 55, 56 may be used to select between month long cycles and cycles of fixed duration (i.e., MONTH or FIXED in fields F5 and F7, respectively). If the FIXED duration option is selected, the display shown in FIG. 30B is displayed. In this display, the user may select the total take days in the fixed cycle. Once this value is selected, the number of take days may be entered in the display shown in FIG. 30C. Upon selection of the number of take days, the user enters today's date in the fixed cycle. As shown in FIG. 30D, the user has entered that today's date is the first day in the fixed cycle.

Figure 30E:
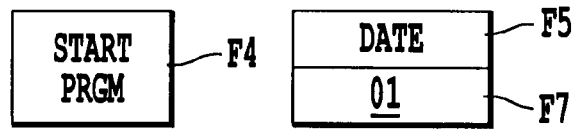
Figure 30F:
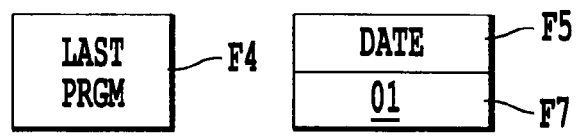

Upon selection of this value, the user may continue editing or saving this information via the EDIT/SAVE display shown in FIG. 27C. FIGS. 30E and 30F illustrate programming the MONTH cycle regimen #7 shown in FIG. 9. As shown, the user enters the first take day of the month in FIG. 30E and upon selection of this value, the user enters the last take day of the month in FIG. 30F. The user is then able to save or continue editing this information as discussed above.

Figure 31A:
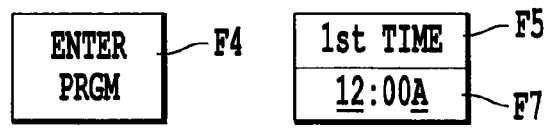
Figure 31B:
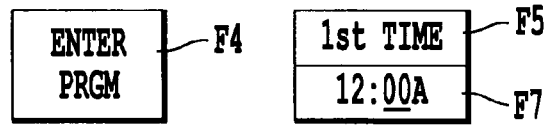
Figure 31C:
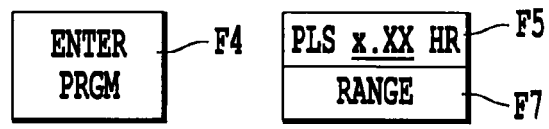
Figure 31D:

FIGS. 31A-31D illustrate operations for programming the custom regimen #0 shown in FIG. 9. As shown, when the custom regimen is selected, the user is able to enter the first time a dose is to be taken as shown in FIGS. 31A and 31B. Preferably, the minute range allowed will not be displayed as earlier than one hour from the previous dose or later within one hour from the first dose of the day. The UP and DOWN keys 55, 56 and SELECT 53 key may be used to scan and select an appropriate take time first by hour then by minute. After the first take time minute is selected, the next earliest take time will be displayed with the hours blinking. Selection of both the hours and minutes indicates the end of dose selection. Entry of the tenth time, entry of a take time on or after 11 PM, or entry 00:00 AM causes the sequence to stop and the information shown in FIG. 31C to be displayed. The UP and DOWN keys 55, 56 may be used to scan the hour in the plus range by 0.25 hours or fifteen minutes, for example. The range allowed is preferably in increments of 0.25 hours and does not exceed the minimum time between two doses. Once the number of plus hours is selected with the SELECT key 53, the information shown in FIG. 31D is displayed.

Again, the user may scan the hour in the minus range by 0.25 hours, for example. The range allowed is preferably in increments of 0.25 hours and does not exceed one quarter the minimum time between two doses or four hours, whichever is less. Once the information is selected, the user may continue editing or save this program as discussed above. Further, note that the plus and minus intervals holds for all settings in a given custom regimen. The minimum interval between two doses is preferably one hour and the minimum plus/minus range is 0.25 hours.

Figure 32A:
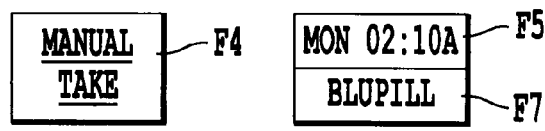
FIGS. 32A-32C illustrate an operation of the MANUAL TAKE sub-menu option.
Figure 32B:

Turning now to the MANUAL TAKE sub-menu option shown in FIG. 32A. The MANUAL TAKE option may be selected by selecting the MED option step S208 in FIG. 11 and then selecting a medication using the PICK MED sub-menu option in FIG. 15A. Selection of these options results in the display shown in FIG. 15A. Selecting the option in FIG. 15E results in the display shown in FIG. 32A and pressing the TAKE 61 key results in the display shown in FIG. 32B. Thus, the user is able to manually take a blue pill at Monday 2:10 AM and record the taking of the same. An alarm2 sounds and returns to an appropriate display after the MANUAL TAKE is recorded. In addition, it is preferable the MANUAL TAKE is operational with all medications irrespective of the ON/OFF status. Utilization of the MANUAL TAKE sequence results in the recording of the event in the nonvolatile memory and in the LAST MEDICATION sub-menu option shown in FIG. 16A. Although it is preferable the default of MANUAL TAKE is disabled when the device is in a lock state, the IR interface may be used so this option is allowed even when the device is locked.

Figure 32C:
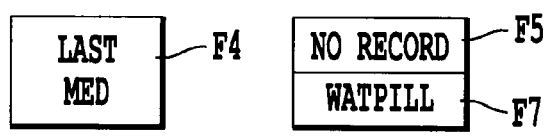

Turning now to FIG. 32C, which illustrates that the data stored as LAST in the display shown in FIG. 16A is updated each time a medication is taken. After a medication take is recorded LAST MED displays the day and time a medication was last taken. When more than 7 days has elapsed since the last dose of medication was taken the display indicates the number of days that have elapsed. The LAST MED display stops giving information about manual takes after 7 days have elapsed.

Figure 33A:
FIGS. 33A-33C illustrate special notifications provided to the user.
Figure 33B:
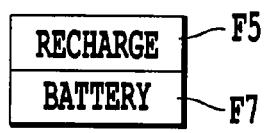
Figure 33C:

FIGS. 33A-33C illustrate special notifications provided to the user including the replacement of the battery in FIG. 33A, recharging of the battery in FIG. 33B and renewing a medication in FIG. 33C. These alarms are displayed in proximity to TAKE and EARLY events, thereby providing the user with other useful information while his or her attention is focused on the device. Thus, the notification for the battery replacement prescription renewal, or battery recharge can be displayed in conjunction with TAKE events. The UP and DOWN keys 55, 56 may be used to scroll between this information.

Figure 34A:
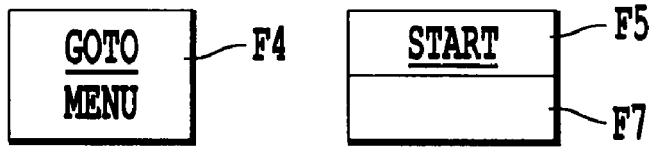
FIGS. 34A-34F illustrate operations performed during a reset operation.
Figure 34B:
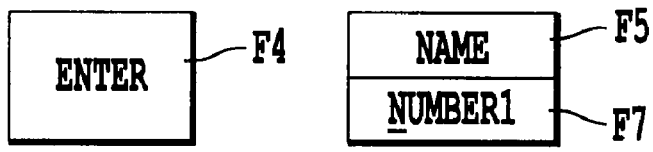
Figure 34C:
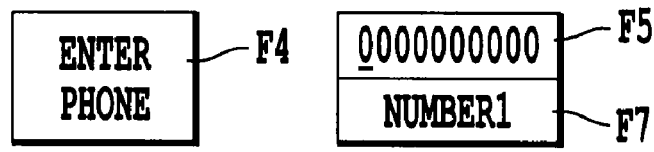
Figure 34D:
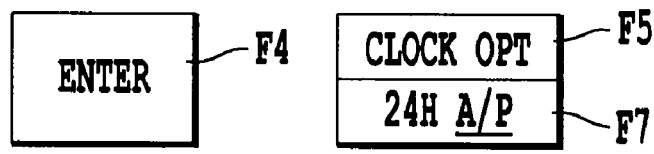
Figure 34E:
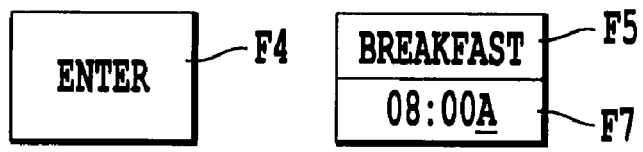
Figure 34F:

FIGS. 34A-34F illustrate operations performed when the RESET 63 key in FIG. 10 is pressed. The RESET 63 key will clear all hand-held unit option settings, TIME is reset to a start of the internal clock with the exception of the setting for the actual user name (which can be changed from the "NAME" user sub-menu option, but will maintain the previously set NAME). The description information entered at the level of the PC and the TAKE event data entries will be maintained. Upon activation of the reset 63 key, the user will be presented with the information shown in FIG. 34A. Only the SELECT 53 key is active at this time. Pressing the SELECT 53 key, the user is requested to enter their name and phone number as shown in FIGS. 34B-34C. The phone number may be entered using the UP and DOWN keys 55, 56 and the SELECT 53 key. Once the information is entered, the user is given the option of editing or saving the entered information as described above. The current DATE and TIME are then set as described above and as shown in FIG. 34D. The desired meal times are also set as shown in FIG. 34E and as described above. As shown in FIG. 34F, "NO TAKES" is displayed in the field F7. Use of the RESET button is not subject to the lock function of the hand-held unit. Further, activation of the RESET function will require use of a paperclip or other similar device and any parameter such as name and phone number as previously entered will not be altered by the RESET function. Note, with this feature a new record will be used with the reset function. Thus if a new user is taking over the device, he or she will be able to enter the new data. However, if the same user was to reset the device, he or she would not need to reenter all information. Any previous events in the EVENT log will also remain saved. Only a single time change (new time) event is logged at the TIME EDIT/SAVE event.

Note that the phrase "make a selection" etc. discussed above corresponds to pressing the SELECT 53 key.

Further, as discussed above, the device includes an IR interface with a PC interface. In conjunction with the interface, the free standing device can download stored information to the PC and the PC will have the capacity to download information to the freestanding unit regarding the operational parameters. The exchange of the data between the free standing unit and the PC can be accomplished in preferably less than one minute when data is being uploaded from the device to the PC and preferably in under 30 seconds when data is being downloaded to the device, for example.

The free standing unit also includes the nonvolatile memory that stores TAKE event information, patient/provider specific information and drug specific information, for example. TAKE event information will include sufficient time data to allow calculation of the day and time when the medication was last taken; a medication identifier and a flag indicating either TAKE, SKIP, MANUAL TAKE or ABORT (time window closes). The nonvolatile memory can store at least 60 days worth of such information and a maximum of 40 events a day, for example, and thus the device will have the capacity to store 60×40=2400 events. Note, that a time change event will use space for two events, and as for a time change event, it is required to store the amount by which the time has changed besides recording the instant at which the time was changed. The memory is preferably non-erasable in the free standing unit, but an option exists to erase TAKE event data via instructions from the PC. Additionally, each free standing unit produced preferably has a unique identifier associated with it.

In addition, patient information entered at the level of the free standing unit includes an eight character alpha/numeric identifier, meal times and a recalculate time, for example. Additional patient specific information can be downloaded from the PC to the device. This data includes a name, an ID number, an additional ID number, a daytime phone number, etc. With regard to the provider, the PC can download the information including an e-mail address, a fax phone number, a group ID number, etc.

Further, drug-specific information includes information that can be generated at the level of the free standing unit and includes a medication acronym, the regimen and the regimen specific parameters as described above. The PC also downloads additional drug-specific data to include a drug name, an NDC number and the medicine strength. Further, note that each free standing unit and software package has a unique identifier that can be stored. At the level of the PC, a mechanism can evaluate any data that conflicts that might exist between the PC and the free standing unit. Further, the PC will be able to command the activation and inactivation of several parameters without any adverse effect on operation of the free standing unit. These parameters include STATUS, MANUAL TAKE, RENEW and SET TIME, for example. The default mode of these parameters is that the feature is DISABLED. In addition to the individual feature control, the LOCK status is required to be in the LOCKED status for the feature to be disabled.

Figure 35A:
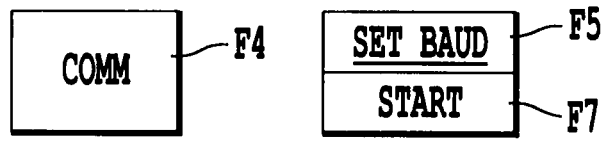
FIGS. 35A-35F illustrate operations for initiating communication with a PC.

Turning now to FIGS. 35A-35F, which illustrates operation for initiating communication with a PC. To communicate with a PC, the device is put in a communication (COMM) mode by pressing the SELECT key 53 in the display shown in FIG. 23F. Upon selection of this sub-menu option, the information shown in FIG. 35A is displayed. The UP and DOWN keys 55, 56 may be used to toggle between the SET BAUD and the START options. If the SELECT key 53 is pressed when the START option is blinking, the device goes into the communication mode and waits for commands from the PC. On an "end of communication command" from the PC, if no command is received for 120 seconds, for example, or the MENU 54 key is pressed, the device drops out of the communication mode and returns to a default screen, for example.

Figure 35B:
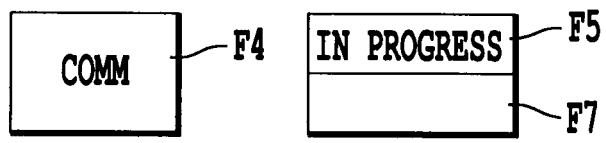
Figure 35C:
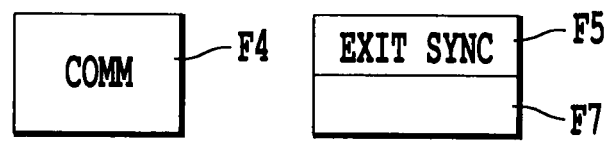
Figure 35D:
Figure 35E:
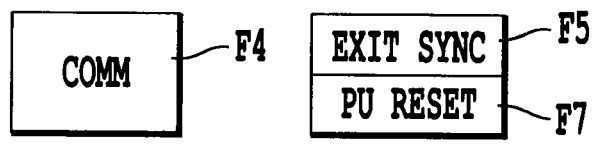
Figure 35F:
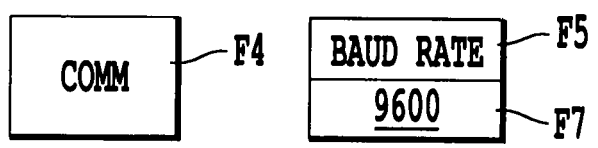

While the device is communicating with the PC, the message shown in FIG. 35B is displayed. At termination of the COMM mode by any means, time out, etc. from the PC or the MENU 54 key, the information shown in FIG. 35C is displayed for at least 2 seconds, for example. During this period, all medications that have been programmed via the IR interface have their take schedules calculated. The information shown in FIGS. 35D and 35E may also be displayed in addition to either the above figures if an attempt to communicate with the PC is made and a low battery condition causes the device to power fail or restart. The display will pass through the IN PROGRESS display shown in FIG. 35D even if it was in EXIT SYNC shown in FIG. 35C already when the power failure occurred. If the SELECT 53 key is pressed when the SET BAUD option is blinking, the display shown in FIG. 35F is presented. The UP and DOWN keys 55, 56 may be used to scroll through a list of appropriate baud rates. A user may then select a desired baud rate.

The event switch shown in the first, second, third and fourth embodiments should be of a size such that activation by an elderly person would not be difficult while at the same time safeguarding against accidental activation. The reset button is of a size such that activation thereof requires a thin, needle-shaped object so as to safeguard against the accidental turning off of the device.

The present invention also includes a time change algorithm, which is implemented to ensure that when a user changes the current time (e.g., due to daylight savings time, etc.), the next TAKE times are appropriately recalculated. That is, changing the clock time in the device, associated with daylight savings times, east to west coast travel, etc., necessitates readjusting as appropriate the various program regimens to assure that the time interval between doses of the medication is appropriately maintained. To achieve this object, an algorithm according to the present invention is implemented to ensure that a minimum time interval is maintained between doses of the medication. The algorithm tests each medication to recalculate a new TAKE time based on the LAST take in conjunction with the time change. For example, the following algorithm may be used:

1) $L_T$=the last time a medication was taken. No take is 0;
2) $K_R$=regimen specific constant; the minimum interval between doses;
3) $T_{NI}$=the first next calculated take time;
4) $T_{NX}$=the next consecutively calculated take time;
5) $N_T$=the operational next take time;
6) $T_D = L_T + K_R$;
7) $N_T = T_{NI}$ if $T_D$ is < or = to $T_{NI}$;
8) $N_T = T_{NX}$ if $T_D$ is < or = to $T_{NX}$;

Thus, if the interval between the last TAKE of the medication and the NEXT take time of the medication is less than or equal to the regimen specific minimal interval constant, the next TAKE is that which has been previously calculated prior to the time change. However, if the interval is less than that specified by the regimen specific interval, a calculation is successively performed with the NEXT calculated take times until the condition is met where the next TAKE time is separate from the last take time by an interval equal to or greater than the regimen specific minimum time interval constant ($K_R$). $K_R$ can vary from regimen to regimen and can have values that preferably range from 1.0 to 0.01 times the time interval between two doses of medication in the regimen. In the current embodiment, the $K_R$ is assigned to the respective regimens as follows:

1/DAY, withFOOD (1 dose per day), emptSTOM (1 dose per day), CYCLE FIXED and CYCLE MONTH—16 hr; 2/D—8 hr: 3/DAY—5 hr; 4/DAY—3 hr; breakfast and dinner withFOOD and emptSTOM—3 hr; D of W, XXHR, and CUST—2/3 times the minimum interval between two doses of medication. The $K_R$ values can be stored permanently in the device or the $K_R$ values specific to a given medication may be assigned by a data entry procedure with the freestanding unit of through the PC-IR interface.

The interval by which the time is changed can also have significant effects on the calculation of time for an appropriate dose of a given medication. For this reason, a constraint that the interval of time change not exceed more than plus or minus 24 hr is established. In the current embodiment, the maximum time change is limited to plus or minus 4 hr. This is because the device offers dosing regimens of greater than 24 hr and because fixed $K_R$ values are assigned on a permanent basis. If these constraints are changed expansion of the time change restraints is possible. The imposition of both the time limit value and the $K_R$ value for calculation are aimed at assuring patient safety by not having the device erroneously advise the patient to take two doses of medication so close together that there is medical danger.

In conjunction with the time change, the time for opening of the early take window is evaluated and if necessary recalculated in compliance with the requirements as set forth below. Note, these calculations are made on the basis of elapsed time.

Adjustment of the early take window according to the present invention is to prevent a situation in which a medication can be taken at a latest point in the early time take window and then in the earliest time in the next take window, which results in the medication being taken in intervals that are too close to each other. In more detail, the prescription compliance device offers the patient the life style latitude to take medication during a time window preceding the calculated take time (early take) and extending to a time after the calculated take time (late take). However, a situation may arise where medication taken at the late take time and then at an early take time violate the minimum interval requirements as defined by the $K_R$ values. For this reason, the time for opening of the early take window after taking a dose of medication is tested and recalculated by application of the following algorithm:

9) $T_E$=the default early window opening time;
10) $E_T$=the operational early opening window time;
11) $E_T=T_D$ if $T_D>T_E$
12) $E_T=T_E$ if $T_D<$ or $=$to $T_E$ Thus, the opening of the early take window is adjusted to the time of the last take plus the value of $K_R$ if this sum produces a time that is later than the default. If the value of the last time plus $K_R$ is earlier than the default, the early window is opened at the default time.

The present invention also relates to a transient take feature. This function is provided by using the IR interface and the PC. For example, a healthcare provider or pharmacist gives the user or patient medication, but wants the patient to begin the medication as soon as possible. Using the transient take feature, the healthcare provider may program the device to begin taking the medication immediately, and then ease into one of the programmed regimens. For example, assume that a child is very ill and requires antibiotics to be taken everyday. If the child was to receive the prescription at 4 pm, for example, and was very ill and needed to take the medication right away, the pharmacist may program the device so as to allow the child to take the antibiotic at 4 PM, and then set the next time to be 10 AM, rather than at the regimen time of 8 AM. On the following day, the regimen could then be implemented so that the child takes the medication at 8 AM every day. Using this feature, the pharmacist may also program the device so that the patient is signaled to take the medication after a certain medical procedure, etc., is completed. For example, assume the patient is to begin taking antibiotics after stitches are removed from a region of the body. Thus, using this feature, the pharmacist or healthcare provider may program the device to begin taking medication in 5 days (after the stitches have been taken out) and to end on a particular date.

In more detail, when the prescription compliance device is programmed by a healthcare provider via the PC interface it may be desirable that take times be set to permit the user to get on a specific schedule or avoid missing a dose of a specific medication. For this reason, the transient take algorithm has been developed for programming specific take times into the device. At the PC, the operator has the opportunity to evaluate the various take events for each medication and determine if the adjustment is desirable. If this is the case, the healthcare provider enters a time at which a dose of medication is to be taken, which is separate from the standard regimen logic. The healthcare provider also has the option to instruct the prescription compliance device to skip one or several of the future take events. The firmware of the prescription compliance device is so structured that it implements these instructions as communicated via the interface.

Figure 36A:
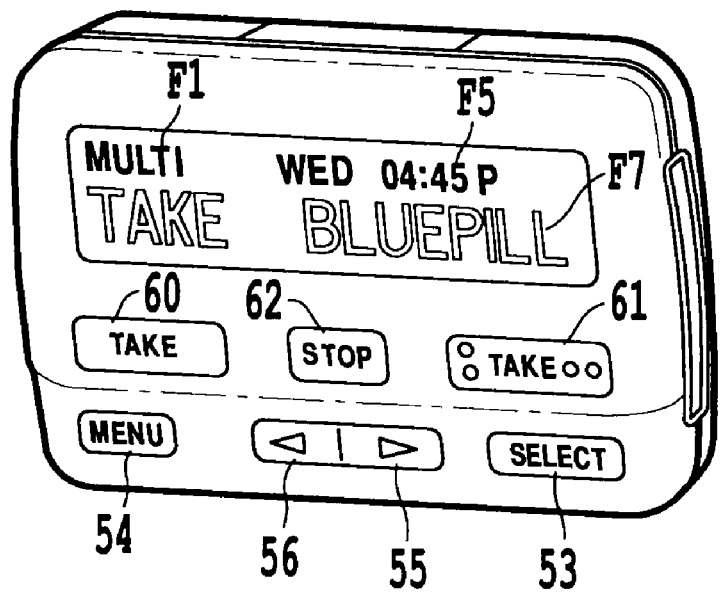
FIGS. 36A-36B respectively illustrate a front view and a side view of the prescription compliance device according to the fourth embodiment.
Figure 36B:
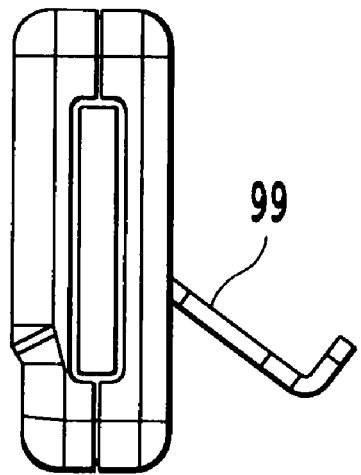

FIGS. 36A-36B illustrate a front view and a side view of the prescription compliance device according to the fourth embodiment, respectively.

As shown in FIG. 36A, the device includes the display fields F1, F5 and F7 similar to that shown in FIG. 10. Also included are the TIME 60 key, SKIP 62 key, TAKE 61 key, MENU 54 key, UP and DOWN keys 55, 56 and the SELECT 53 key. FIG. 36B illustrate a fold out stand 99 that puts the device at a convenient viewing angle. Note that the embodiment shown in FIGS. 36A-36B differ from the device shown in FIGS. 8A-8C in that the device shown in FIGS. 36A-36B is a free standing device and is not attached to the medication bottle, for example.

The present invention may also be used to gather medical information. Through the PC interface, appropriate medical emergency information such as the name of physicians, relations and healthcare providers and appropriate contact information, the patients medical status including medical conditions, medical history, allergies, and any other information which might be of value to the healthcare provider in an emergency situation may be entered. It is also possible to access this information either at the level of the device itself or though the PC interface.

People currently use a variety of electronic aids such as personal digital assistants, cellular telephones, pocket calculators, music storage, reproduction and receiving devices, etc. According to the present invention, the functions of the prescription compliance device may be integrated with a cellular telephone. Such a medi-phone provides users with the option of having both a cellular telephone and the prescription compliance device to carry around as a single unit. Not only would this provide better convenience, but it provides the user with significant cost savings since components such as case, LCD, battery, charger, electronic circuit components and microprocessors may be shared between the two functionalities.

Another feature includes combining the prescription compliance device with a personal digital assistant. The advantages of this is similar to those afforded by combination with the telephone. It is also be possible to integrate the cellular telephone, personal digital assistant and the prescription compliance device as a single unit with even greater advantages and savings. Similarly combination of the prescription compliance device with personal musical devices provide advantages.

The multi-use device is particularly advantageous in that implementing the features of the prescription compliance device within in a phone, etc. hides the fact that the person is taking the medication. That is, for people with diseases such as Aids, several medications must be taken during the day. Thus, if an ill person was in a public area (such as a train station), for example, it would be obvious to everyone within the vicinity that the person was using a medication device. However, according to the present invention, the medication functions of the programming compliance device may be implemented within the cellular phone. This hides the fact that the person is taking medication and is less embarrassing. Further, an elderly person may not be interested in having a cell phone, which can be problematic for a son or daughter, etc. who wishes to determine the status of their elderly parents throughout the day. That is, many elderly people may find cell phones to be not necessary. However, according to the present invention, the programming options of the prescription compliance device may be integrated within the cell phone, which will then make the elderly person who does not want a cell phone, to use the cell phone as a prescription compliance device. Thus, because the elderly person now use the cell phone, it will be easier to stay in contact with them. This also results in the cellular manufacturers, selling more cell phones.

In addition, the present invention also is particularly advantageous in that it logs information, which is medical information or any other information. That is, the device can be set so that it alerts someone that an action must be taken, and the alarms may be set using the preset regimens or may be set using the custom regimen. The actions scheduled may include the gathering of some data. In a medical scenario, it may be taking the temperature, blood glucose, blood pressure, pulse rate or other similar things that require entry of numeric and/or alphabetic data. For example, assume that the physician wishes the patient to take their blood pressure one hour after taking a Viagra pill. According to the prescription compliance device of the present invention, an alarm may be set alerting the person to take their blood pressure or gather other data.

The device also provides the user the opportunity to enter relevant data. Procedures similar to those used for entering the name and phone numbers discussed above may be used for this purpose. The data thus routinely logged may also be downloaded to the PC for analysis. Alternatively, the log data may be viewed using the device (i.e., using the event log function). In addition to entering data, the device is capable of storing lists that can be reviewed and a yes or no answer can be provided and is logged. Medically, this could be done for things such as a headache, back pain, sore arm etc. That is, the user is able to enter possible side effects related to the medication, which may then be used to analyze different side effects for different people. In addition, for a watchman it could be to open, light on, alarm set, etc. The options can be tiered to make access easy through GI, neurologic, vascular, and items may be selected and then sub items addressed. Data from this feature can be prompted, logged and handled in a manner similar to that discussed above. Further, data entry protocols may be stored in the firmware of the device. Alternatively, the capacity of data entry may be stored in the firmware of the device and then tailored by using a PC. An alarm could alert the user to enter numeric data. The PC will then specify a screen display to indicate what data is to be entered and then provide a field in which to make the numeric entry. With menu driven data, the user would be alerted to enter information regarding a topic and then be taken through a menu similar to the menus discussed above.

Electronic Configuration and Programming Parameters

This invention may be conveniently implemented using a conventional general purpose digital computer or microprocessor programmed according to the teachings of the present specification, as will be apparent to those skilled in the computer art. Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art.

The present invention includes a computer program product which is a storage medium including instructions which can be used to program a computer to perform a process of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

Obviously, numerous modifications and variations of the present invention are possible in light of the above teachings. The specific parameters mentioned in conjunction with the description of the invention have been set forth solely for illustrative purposes and are not limiting of the scope of the invention in any way. It is therefore to be understood that within the scope of appended claims, the invention may be practiced otherwise than as specifically described herein.

The invention claimed is:

1. A method for monitoring patient compliance to medical therapy, comprising:
    repeatedly measuring therapy compliance of a patient and storing such information on a device;
    uploading the therapy compliance measurements stored on the device to a computing unit;
    evaluating patient compliance based on the uploaded therapy compliance measurements;
    identifying instances where patient compliance fails to meet predetermined compliance requirements; and
    sending a notification, about one or more instances, to a party based on patient compliance whereby action can be taken by that party.

2. The method according to claim 1, further comprising:
    using a computer to conduct the evaluating.

3. The method according to claim 1, the sending comprising:
    sending the notification over a network.

4. The method according to claim 1, further comprising:
    scheduling and uploading therapy regimens into the device over a network.

5. The method according to claim 4, comprising:
    scheduling and uploading therapy regimens into the device over a network from a health care provider or health care professional.

6. The method according to claim 5, wherein the therapy regimens include using medication with food within a time range of approximately 15 minutes before food intake to 60 minutes after food intake.

7. The method according to claim 6, wherein the therapy regimens include using medication without food within a time range of at least 30-60 minutes before food intake and 120-180 minutes after food intake.

8. The method according to claim 7, wherein the therapy regimens include a requirements that there be a minimum of 4 hours between first food intake of a day and second food intake of the day, that there be a minimum of 5 hours between second food intake of the day and third food intake of the day and the first, second and third food intakes must be completed within 14 hours.

9. The method according to claim 5, wherein the therapy regimens include monthly cycle, fixed cycle or As-need cycle type regimens.

10. The method according to claim 9, wherein the monthly cycle is based on a perpetual calendar and is calculated using a time of day for a "take" and a start and stop data in a month in which medication is to be used.

11. The method according to claim 9, wherein the fixed cycle is a regimen in which a duration of a cycle is set and is counted from a first day of the cycle.

12. The method according to claim 9, wherein the As-needed cycle requires that medication only be taken after a minimum interval has passed, the minimum interval until a next dose is calculated at a time of medication use.

13. The method according to claim 1, further comprising:
    scheduling and uploading therapy regimens into the device locally at the device.

14. The method according to claim 4, wherein calculations needed for therapy regimens are performed locally at the device.

15. The method according to claim 4, wherein calculations needed for therapy regimens are executed prior to uploading the therapy regimens into the device.

16. The method according to claim 4, wherein the device is able to perform calculations needed for therapy regimens locally or receive therapy regimens which have been previously calculated.

17. The method according to claim 1, wherein the device includes a skip function enabling a user to decline therapy in response to a local device alert, the execution of the skip function resulting in a recordation in the device.

18. The method according to claim 1, wherein the device includes a take function enabling a user to accept therapy in response to a local device alert, the execution of the take function resulting in a recordation in the device.

19. The method according to claim 1, wherein the device generates a missed therapy event when no skip or take function is entered in response to a local device alert, the generation of the missed therapy event resulting in a recordation in the device.

20. The method according to claim 1, wherein a number of doses required for a trip is calculated by a trip algorithm within the device that requires entry of a start and stop date for the trip and on this basis a need for refill during the trip is calculated.

21. The method according to claim 4, wherein the device includes a time change means that adjusts the therapy regimens based on a time change.

22. The method according to claim 20, wherein the device includes an early takes means for dealing with early execution of a take function using information regarding the trip.

23. The method according to claim 1, wherein the device includes a cellular phone.

24. The method according to claim 1, wherein the device is a PDA.

25. The method according to claim 1, wherein the device includes a personal music player.

26. The method according to claim 1, wherein the device includes a personal music player and a cellular phone.

27. The method according to claim 1, wherein the device is configured to receive SMS, WIFI or wireless communications.

28. The method according to claim 1, wherein the device is a gaming device.

29. The method according to claim 1, wherein the device is a pager.

\* \* \* \* \*